United States Patent [19]

Cate et al.

[11] Patent Number: 5,047,336
[45] Date of Patent: Sep. 10, 1991

[54] DNA SEQUENCES, RECOMBINANT DNA MOLECULES AND PROCESSES FOR PRODUCING MULLERIAN INHIBITING SUBSTANCE-LIKE POLYPEPTIDES

[75] Inventors: Richard L. Cate, Brookline; Patricia K. Donahoe, Weston, both of Mass.

[73] Assignees: Biogen, Inc., Cambridge; The General Hospital Corporation, Boston, both of Mass.

[21] Appl. No.: 792,880

[22] Filed: Oct. 30, 1985

[51] Int. Cl.⁵ .................. C12N 1/21; C12N 1/16; C12N 15/10; C12N 5/16; C12N 15/70; C12N 15/74; C12N 15/79
[52] U.S. Cl. .................. 435/69.4; 435/69.1; 435/70.1; 435/71.1; 435/91; 435/172.1; 435/172.3; 435/240.2; 435/252.3; 536/27; 935/9; 935/29; 935/32; 935/34; 935/38; 935/56; 935/57; 935/60; 935/66
[58] Field of Search .................. 435/317, 68, 70, 91, 435/172.3, 240, 320, 253; 935/9, 29, 32, 34, 38, 56, 57, 60; 536/27

[56] References Cited

U.S. PATENT DOCUMENTS

| 4,404,188 | 9/1983 | Donahoe et al. | 424/105 |
| 4,442,205 | 4/1984 | Hamer et al. | 435/68 |
| 4,487,833 | 12/1984 | Donahoe et al. | 435/172.2 |
| 4,510,131 | 4/1985 | Donahoe et al. | 424/105 |
| 4,740,587 | 4/1988 | Ling et al. | 530/3.3 |

OTHER PUBLICATIONS

Jaye et al. (1983), Nucleic Acids Res. 11: 2335–45.
P. Donahoe et al., Recent Progress in Hormone Research, 38, 279–330 (1982).
P. Donahoe et al., Ann. Rev. Physiol., 46, 53–65 (1984).
G. Budzik et al., Cell, 34, 307–314 (1983).
Chemical Week, Jan. 30, 1985, p. 69.
SCRIP, No. 976, p. 22, Feb. 25, 1985.
J-Y Picard et al., "Purification of Testicular AntiMullerian Hormone Allowing Direct Visualization of the Pure Glycoprotein and Determination of Yield and Purification Factor", Molecular and Cellular Endocrinology, 34, pp. 23–29 (1984) [Picard et al., III].
A. Fuller, Jr. et al., "Mullerian Inhibiting Substance Inhibits Colony Growth of a Human Ovarian Carcinoma Cell Line", J. Clin. Endocr. Met., 54, 1051–1055 (1982) [Fuller et al. I].
A. Fuller, Jr. et al., "Mullerian Inhibiting Substance Inhibition of a Human Endometrial Carcinoma Cell Line Xenografted in Nude Mice", Gynecologic Oncology, 17, 124–132 (1984) [Fuller et al. II].
A. Fuller, Jr. et al., "Mullerian Inhibiting Substance Reduction of Colony Growth of Human Gynecologic Cancers in a Stem Cell Assay", Gynecologic Oncology, 22, 135–148 (1985) [Fuller et al. III].
M. Hayashi et al., "Immunocytochemical Localization of Mullerian Inhibiting Substance in the Rough Endoplasmic Reticulum and Golgi Apparatus in Sertoli Cells of the Neonatal Calf Testis Using a Monoclonal Antibody", Journal of Histochemistry and Cytochemistry, 32, 649–654 (1984).
J. Hutson et al., "The Ontogeny of Mullerian Inhibiting Substance in the Gonads of the Chicken", J. Pediatric Surgery, 16, 822–827 (1981) [Hutson et al. I].
J. Hutson et al., "Phosphorylation Events During Mullerian Duct Regression", Science, 223, 586–589, (1984) [Hutson et al., II].
J. Hutson et al., "Steroid Modulation of Mullerian Duct Regression in the Chick Embryo", General and Comparative Endocrinology, 57, 88–102 (1985) [Hutson et al. III].

(List continued on next page.)

Primary Examiner—Richard A. Schwartz
Assistant Examiner—Richard C. Peet
Attorney, Agent, or Firm—James F. Haley, Jr.; Margaret A. Pierri; Linda A. Wadler

[57] ABSTRACT

DNA sequences coding for at least one MIS-like polypeptide, recombinant DNA molecules comprising such sequences, hosts comprising such sequences and processes for producing such polypeptides in hosts transformed with those DNA sequences. The MIS-like polypeptides are useful in the treatment of ovarian cancer and other susceptible cancers.

15 Claims, 25 Drawing Sheets

Bovine tryptic peptides used for making oligonucleotide probes

Peak # T105-106:

LeuAspLeuValProPheProGlnPro

Peak # T81:

LeuAlaLeuAspProGlyAlaLeuAlaGlyPheProGlnGlyGlnVal

OTHER PUBLICATIONS

H. Iwaka et al., "Steroid Enhancement of Mullerian Duct Regression", *J. Pediatric Surgery*, 17, 453-458 (1982) [Ikawa et al. I].

H. Ikawa et al., "Cyclic Adenosine 3',5'-Monophosphate Modulation of Mullerian Duct Regression", *Endocrinology*, 114, 1686-1691 (1984) [Ikawa et al. II].

N. Josso, "Permeability of Membranes to the Mullerian-Inhibiting Substance Synthesized by the Human Fetal Testis in Vitro: A Clue to its Biochemical Nature", *J. Clin. Endocr.*, 34, 265-270 (1972) [Josso I].

N. Josso, "In Vitro Synthesis of Mullerian-Inhibiting Hormone by Seminiferous Tubules Isolated from the Calf Fetal Testis", *Endocrinology*, 93, 829-834 (1973) [Josso II].

N. Josso et al., "Mullerian-Inhibiting Activity of Calf Fetal Testes: Relationship to Testosterone and Protein Synthesis", *Biology of Reproduction*, 13, 163-167 (1975).

D. MacLaughlin et al., "Specific Estradiol Binding in Embryonic Mullerian Ducts: A Potential Modulator of Regression in the Male and Female Chick", *Endocrinology*, 113, 141-145 (1983).

M. Mudgett-Hunter et al., "Monoclonal Antibody to Mullerian Inhibiting Substance", *Journal of Immunology*, 128, 1327-1333 (1982).

J-Y. Picard et al., "Anti-Mullerian Hormone: Estimation of Molecular Weight by Gel Filtration", *Biomedicine*, 25, 147-150 (1976) [Picard et al. I].

J-Y Picard et al., "Biosynthesis of Labelled Anti-Mullerian Hormone by Fetal Testes: Evidence for the Glycoprotein Nature of the Hormone and for its Disulfide-Bonded Structure", *Molecular and Cellular Endocrinology*, 12, 17-30, (1978) [Picard et al. II].

Z. Rosenwaks et al., "In Vitro Inhibition of Endometrial Cancer Growth by a Neonatal Rat Testicular Secretory Product", *J. Clin. Endocr. Met.*, 52, 817-819 (1981).

H. Shima et al., "Production of Monoclonal Antibodies for Affinity Purification of Bovine Mullerian Inhibiting Substance Activity", *Hybridoma*, 3, 201-214 (1984).

D. Swann et al., "Extraction of Mullerian Inhibiting Substance from Newborn Calf Testis", *Developmental Biology*, 69, 73-84 (1979).

B. Vigier et al., "A Monoclonal Antibody Against Bovine Anti-Mullerian Hormone", *Endocrinology*, 110, 131-137 (1982) [Vigier et al. I].

B. Vigier et al., "Production of Anti-Mullerian Hormone: Another Homology Between Sertoli and Granulosa Cells", *Endocrinology*, 114, 1315-1320 (1984) [Vigier et al. II].

M. G. Blanchard et al., "Source of the Anti-Mullerian Hormone Synthesized by the Fetal Testis: Mullerian-Inhibiting Activity of Fetal Bovine Sertoli Cells in Tissue Culture", *Pediat. Res.*, 8, 968-971 (1974).

G. Budzik et al., "Enhanced Purification of Mullerian Inhibiting Substance by Lectin Affinity Chromatography", *Cell*, 21, 909-915 (1980) [Budzik et al. I].

G. Budzik et al., "A Possible Purification of Mullerian Inhibiting Substance and a Model for Its Mechanism of Action", *Developmental Mechanisms: Normal and Abnormal*, 171, 207-223 (1985) [Budzik et al. II].

P. Donahoe et al., "The Production of Mullerian Inhibiting Substance by the Fetal, Neonatal and Adult Rat", *Biology of Reproduction*, 15, 329-334 (1976) [Donahoe et al. I].

P. Donahoe et al., "Mullerian Inhibiting Substance Activity in Bovine Fetal, Newborn and Prepubertal Testes", *Biology of Reproduction*, 16, 238-243 (1977) [Donahoe et al. II].

P. Donahoe et al., "Mullerian Inhibiting Substance in Human Testes After Birth", *Journal of Pediatric Surgery*, 12, 323-330 (1977) [Donahoe et al. III].

P. Donahoe et al., "Mullerian Duct Regression In The Embryo Correlated with Cytotoxic Activity Against Human Ovarian Cancer", *Science*, 205, 913-915 (1979) [Donahoe et al. IV].

P. Donahoe et al., "Mullerian Inhibiting Substance Inhibits Growth of a Human Ovarian Cancer In Nude Mice", *Ann. Surg.*, 194, 472-480 (1981), [Donahoe et al. V].

P. Donahoe et al., "The Biochemistry and Biology of Mullerian Inhibiting Substance", *Pediatric Andrology*, 37-46, 1981 [Donahoe et al. VI].

P. Donahoe et al., "Mullerian-Inhibiting Substance: An Update", *Recent Progress in Hormone Research*, 38, 279-330 (1982), [Donahoe et al. VII].

P. Donahoe et al., "Mechanism of Action of Mullerian Inhibiting Substance", *Ann. Rev. Physiol.*, 46, 53-65 (1984), [Donahoe et al. VIII].

P. Donahoe et al., "Molecular Dissection of Mullerian Duct Regression", *The Role of Extracellular Matrix in Development*, 573-595 (1984) [Donahoe et al. IX].

M. Fallat et al., "The Role of Nucleotide Pyrophosphatase in Mullerian Duct Regression", *Developmental Biology*, 100, 358-364 (1983) [Fallat et al. I].

M. Fallat et al., "Androgen Stimulation of Nucelotide Pyrophosphatase During Mullerian Duct Regression", *Endocrinology*, 144, 1592-1598 (1984) [Fallat et al. II].

FIG. 1

Bovine tryptic peptides used for making oligonucleotide probes

Peak # T105-106: LeuAspLeuValProPheProGlnPro

Peak # T81: LeuAlaLeuAspProGlyAlaLeuAlaGlyPheProGlnGlyGlnVal

FIG. 2

Oligonucleotide probes

OLIGOMER POOL 1 - 4 :  256 degenerate 17mer made from tryptic peptide T105-106 synthesized in four subpools of 64 fold degeneracy

```
     Val Pro Phe Pro Gln Pro
5'   GTN CCN TTY CCN CAR CC  3'
3'   CAN GGN AAR GGN GTY GG  5'
```

| subpool sequence | subpool # | degeneracy |
|---|---|---|
| 3' CAN GGA AAR GGN GTY GG  5' | 1 | 64 |
| 3' CAN GGG AAR GGN GTY GG  5' | 2 | 64 |
| 3' CAN GGT AAR GGN GTY GG  5' | 3 | 64 |
| 3' CAN GGC AAR GGN GTY GG  5' | 4 | 64 |

OLIGOMER POOL 9 - 12:  512 fold degenerate 20mer made from tryptic peptide T81 synthesized in four subpools of 128 fold degeneracy

```
     Gly Phe Pro Gln Gly Gln Val
5'   GGN TTY CCN CAR GGN CAR GT  3'
3'   CCN AAR GGN GTY CCN GTY CA  5'
```

| subpool sequence | subpool # | degeneracy |
|---|---|---|
| 3' CCN AAR GGA GTY CCN GTY CA  5' | 9 | 128 |
| 3' CCN AAR GGG GTY CCN GTY CA  5' | 10 | 128 |
| 3' CCN AAR GGT GTY CCN GTY CA  5' | 11 | 128 |
| 3' CCN AAR GGC GTY CCN GTY CA  5' | 12 | 128 |

FIG. 2(cont'd)

BREAKDOWN OF SUBPOOL 2: 64 fold degenerate 17mer synthesized in four subpools of 16 fold degeneracy

3' CAN GGG AAR GGN GTY GG 5'

| subpool sequence | subpool # | degeneracy |
|---|---|---|
| 3' CAN GGG AAR GGA GTY GG 5' | 13 | 16 |
| 3' CAN GGG AAR GGG GTY GG 5' | 14 | 16 |
| 3' CAN GGG AAR GGT GTY GG 5' | 15 | 16 |
| 3' CAN GGG AAR GGC GTY GG 5' | 16 | 16 |

BREAKDOWN OF SUBPOOL 12: 128 fold degenerate 20mer synthesized in four subpools of 32 fold degeneracy

3' CCN AAR GGC GTY CCN GTY CA 5'

| subpool sequence | subpool # | degeneracy |
|---|---|---|
| 3' CCN AAR GGC GTY CCA GTY CA 5' | 17 | 32 |
| 3' CCN AAR GGC GTY CCG GTY CA 5' | 18 | 32 |
| 3' CCN AAR GGC GTY CCT GTY CA 5' | 19 | 32 |
| 3' CCN AAR GGC GTY CCC GTY CA 5' | 20 | 32 |

FIG. 3A   DNA SEQUENCE OF BOVINE MIS GENE — GENOMIC/cDNA FUSION

```
     CAAGGTCATGTCCCAGGAGGATAGGGACCGCCCTGCACCACAAACAGC
  1  ------+---------+---------+---------+---------+   50
     GTTCCAGTACAGGGTCCTCCTCTATCCCTGGCGGGACGTGGTGTTTGTCG

TCTGCTCCCTCTTATAAAGTAGGGCAGCCCAGCCCCCTGGAAGCTCCCAGG
 51  ------+---------+---------+---------+---------+   100
     AGACGAGGGAGAATATTTCATCCCGTCGGGGTCGGGGACCTTCGAGGGTCC

ATGCCCGGTCCATCTCTCTGGCCCTGGTGCTGTCGGCCATGGGGGC
101  ------+---------+---------+---------+---------+   150
     TACGGGCCAGGTAGAGAGACCGGACCACGACAGCCGGTACCCCCG

M  P  G  P  S  L  S  L  A  L  V  L  S  A  M  G  A

TCTGCTGAGGCCAGGGACCCCCAGGGAAGAAGTCTTCAGCACCTCAGCCT
151  ------+---------+---------+---------+---------+   200
     AGACGACTCCGGTCCCTGGGGGTCCCTTCTTCAGAAGTCGTGGAGTCGGA

L  L  R  P  G  T  P  R  E  E  V  F  S  T  S  A  L

TGCCCAGGGAGCAGGCCACAGGCCAGCGGGCACTCATCTTTCAGCAAGCC
201  ------+---------+---------+---------+---------+   250
     ACGGGTCCCTCGTCCGGTGTCCGGTCGCCCGTGAGTAGAAAGTCGTTCGG

```
     TGGGACTGGCCACTCTCTCCAGTCTCTGGCTGCCAGGCAGCCCTCTGGACCC
251  ---------+---------+---------+---------+---------+  300
     ACCCTGACCGGTGAGAGAGGTCAGAGACCGACGGTCCGTCGGGAGACCTGGG

W  D  W  P  L  S  S  L  W  L  P  G  S  P  L  D  P

CCTGTGCCTGGTGACCCTGCATGGGAGTGGCAACGGGAGCAGGGCCCCCC
301  ---------+---------+---------+---------+---------+  350
     GGACACGGACCACTGGGACGTACCCTCACCGTTGCCCTCGTCCCGGGGGG

L  C  L  V  T  L  H  G  S  G  N  G  S  R  A  P  L

TGCGGGTGGTGGGGTCCTGAGCAGCTACGAGCAGGCCTTCCTGGAGGCT
351  ---------+---------+---------+---------+---------+  400
     ACGCCCACCACCCCCAGGACTCGTCGATGCTCGTCCGGAAGGACCTCCGA

R  V  G  V  L  S  S  Y  E  Q  A  F  L  E  A

GTGCGGGGCACCCACCTGGGGCCTGAGTGACTTGACCACCTTCGCAGTGTG
401  ---------+---------+---------+---------+---------+  450
     CACGCCCCGTGGGTGGACCCCGGACTCACTGAACTGGTGGAAGCGTCACAC

V  R  R  T  H  W  G  L  S  D  L  T  T  F  A  V  C

CCCCGCTGGCAACGGGCAGCCTGTGCTGCCCCACCTGCAGCGGCTGCAGG
451  ---------+---------+---------+---------+---------+  500
     GGGGCGACCGTTGCCCGTCGGACACGACGGGGTGGACGTCGCCGACGTCC

```
     CATGGCTGGGGAGCCCGGGGGCGGTGGCTGGTGGTCCTGCACCCTGGAG
501  ------------------------------------------------  550
     GTACCGACCCCCTCGGGCCCCCGCCACCGACCACCAGGACGTGGACCTC

W  L  G  E  P  G  G  R  W  L  V  V  L  H  L  E

GAAGTGACGTGGGAGCCAACACCCTTGCTGAGGTTCCAGGAGCCTCCGCC
551  ------------------------------------------------  600
     CTTCACTGCACCCTCGGTTGTGGGAACGACTCCAAGGTCCTCGGAGGCGG

E  V  T  W  E  P  T  P  L  L  R  F  Q  E  P  P  P

TGGAGGAGCCAGCCCCCCAGAGCTGGCTGCTGTGGTGTACCCAGGGC
601  ------------------------------------------------  650
     ACCTCCTCGGTCGGGGGGTCTCGACCGACGACACCACAGGTCCCG

G  G  A  S  P  P  E  L  A  L  L  V  V  V  P  G  P

CTGGCCTGGAGGTCACTGTCACCGGGCTACCTGGCACCCAGAGC
651  ------------------------------------------------  700
     GACCGGACCTCCAGTGACAGTGGCCCCGACCGATGGACCGTGGGTCTCG

G  L  E  V  T  V  T  G  A  G  L  P  G  T  Q  S

CTCTGCCTGACCGCGGACTCGGACTTCCTGGCCTTGGTTGTCGTGGACCACCC
701  ------------------------------------------------  750
     GAGACGGACTGGCGCCTGAGCCTGAAGGACCGGAACCAGCACCACCTGGTGGG

```
       GGAGGGGGCCTGGCGCCGGCCTGGGTTAGCCCTTACCCTGCGGCCCGTG
751    ------+---------+---------+---------+---------+ 800
       CCTCCCCCGGACCGCGGCCGGACCCAATCGGGAACGCCGGGCAC

E  G  A  W  R  R  P  G  L  A  L  T  L  R  R  R  G

GAAATGGTGCGCTCCTGAGCACTGCCCAGCTGCAGGCGCTGCTGTTCGGT
801    ------+---------+---------+---------+---------+ 850
       CTTTACCACGCGAGGACTCGTGACGGGTCGACGTCCGCGACAAGCCA

N  G  A  L  L  S  T  A  Q  L  Q  A  L  L  F  G

GCGGACTCCCGCTGCTTCACACGAAAGACCCCAGCCCTTGTTACTCTTGCT
851    ------+---------+---------+---------+---------+ 900
       CGCCTGAGGGCGACGAAGTGTGCTTTCTGGGGTCGGGACAATGAGAACGA

A  D  S  R  C  F  T  R  K  T  P  A  L  L  L  L

GCCGGGCCCGGTCTCTTGCGGCACCGATGCCCGCGACGGTCGGCTGGACTTGG
901    ------+---------+---------+---------+---------+ 950
       CGGCCCGGGCCAGAGAAGCCGTGGCTACGGGCGCTGCCAGCCGACCTGAACC

P  A  R  S  S  A  P  M  P  A  H  G  R  L  D  L  V

TGCCCTTCCCGCAGCCCAGGGCTTCCCCGAGCCCAGAGAGGAGCACCGCCC
951    ------+---------+---------+---------+---------+ 1000
       ACGGGAAGGGCGTCGGGTCCCGAAGGGCCTCGGTCTCCTCCGTGGCGGG

P  F  P  Q  P  R  A  S  P  E  P  E  E  A  P  P
```

```
1001 AGCGCTGATCCCTTCCTGGAGACTCTCACGCGCCTGGTGCGCGCTTGC
     ----+----+----+----+----+----+----+----+----+ 1050
     TCGCGACTAGGGAAGGACCTCTGAGAGTGCGCGGACCACGCGCGAACG
      S  A  D  P  F  L  E  T  L  T  R  L  V  R  A  L  A

GGGACCCCCGGCCCGAGCCTCGCCACCGGCCTGGCCTTGGACCCGGGCG
1051 ----+----+----+----+----+----+----+----+----+ 1100
     CCCTGGGGGCCGGGCTCGGAGCGGTGGCCGGACCGGAACCTGGGCCCGC
      G  P  P  A  R  A  S  P  P  R  L  A  L  D  P  G  A

CACTGGCTGGTTTCCGCAGGGCCAGGTCAACCTGTCGGACCCCGCGGCC
1101 ----+----+----+----+----+----+----+----+----+ 1150
     GTGACCGACCAAAGGGCGTCCCGGTCCAGTTGGACAGCCTGGGGCGCCGG
      L  A  G  F  P  Q  G  Q  V  N  L  S  D  P  A  A

CTGGAGCGCCTGCTGGACGGGGAGGAGCCGCTGCTCCTGCTGCTGCCGCC
1151 ----+----+----+----+----+----+----+----+----+ 1200
     GACCTCGCGGACGACCTGCCCCTCCTCGGCGACGACGACGACGGCGG
      L  E  R  L  L  D  G  E  E  P  L  L  L  L  L  P  P

GACGGCAGCCACCACCGGGGTCCCCGCAACGCCGCAAGGTCCCAAGTCCC
1201 ----+----+----+----+----+----+----+----+----+ 1250
     CTGCCGTCGGTGGTGGCCCCAGGGGCGTTGCGGCGTTCCAGGGTTCAGGG
      T  A  A  T  T  G  V  P  A  T  P  Q  G  P  K  S  P
```

```
1251 CTCTGTGGGCCGCGGGACTAGCGCGGGCCGGGTGGCTGCCGAGCTTCAGGCG
     ---------+---------+---------+---------+---------+ 1300
     GAGACACCCGGCGCCCTGATCGCGCCCACCGACGGCTCGAAGTCCGC

L  W  A  A  G  L  A  R  R  V  A  A  E  L  Q  A

1301 GTGGCCGCCGAGCTGCGTGCCCTCCCGGGCCTGCCTCCAGCTGCCCCACC
     ---------+---------+---------+---------+---------+ 1350
     CACCGGCGGCTCGACGCACGGGAGGGCCCGACGGAGGTCGACGGGGTGG

V  A  A  E  L  R  A  L  P  G  L  P  P  A  A  P  P

1351 GCTGCTGGCGCGCCTGCTGGCACTGTGCCCGGGAAACCCAGACAGCCCCG
     ---------+---------+---------+---------+---------+ 1400
     CGACGACCGCGCGGACGACCGTGACACGGGCCCTTTGGGTCTGTCGGGGC

L  L  A  R  L  L  A  L  C  P  G  N  P  D  S  P  G

1401 GCGGGCCCCGTGCTGCCGCGCGCTGCTGCTCAAAGGCTGCAGGGCCTGCGC
     ---------+---------+---------+---------+---------+ 1450
     CGCCCGGGGCACGACGGCGCGCGACGACGAGTTTCGACGTCCCGGACGCG

G  P  L  R  A  L  L  L  K  A  L  Q  G  L  R

1451 GCTGAGTGGCGCGGGCGGGAGCGGGAGCTCTGCACGGGCCAGCCAG
     ---------+---------+---------+---------+---------+ 1500
     CGACTCACCGCGCCCCGCCCTCGCCCTCGAGACGTGCCCGGTCGGTC

A  E  W  R  G  R  E  R  S  G  S  A  R  A  Q  R  S
```

```
1501 CGCCGGGGCCGCGGGGCTGCAGAGACGGGGCCGTGCTCTGCGTGAGCTGAGCG
     GCGGCCCCGGCGCCCGACGTCTGCCCGGCACGGAGACGCACTCGACTCGC     1550
      A  G  A  A  A  A  D  G  P  C  A  L  R  E  L  S  V

1551 TAGACCTGCGGGCCGAGGCGCTCGGTGCTCATCCCGAGACATACCAGGCC
     ATCTGGACGCCCGGCTCCGGAGCCACGAGTAGGGGCTCTGTATGGTCCGG    1600
      D  L  R  A  E  R  S  V  L  I  P  E  T  Y  Q  A

1601 AACAACTGCCAGGGGCCTGCGGCCCTCAGTCGGACCGCAACCCGCG
     TTGTTGACGGTCCCCGGACGCCGAGTCAGCCTGGCGTTGGGCGC         1650
      N  N  C  Q  G  A  C  G  W  P  Q  S  D  R  N  P  R

1651 CTACGGCAACCACGTGGTGCTGCTAAAGATGCAGGCCCGCGGCCA
     GATGCCGTTGGTGCACCACGACGATTTCTACGTCCGGGCGCCGGT        1700
      Y  G  N  H  V  V  L  L  L  K  M  Q  A  R  G  A  T

1701 CCCTGGCGCGCCCGCCCTGCTGTGCCCACAGCCTACACCGGCAAGCTC
     GGGACCGCGCGGGGACGACACACGGGTGTCGGATGTGGCCGTTCGAG      1750
      L  A  R  P  P  C  C  V  P  T  A  V  T  G  K  L
```

```
1751 CTCATCAGCCTGTCCGAGGAGCGCATCAGTGCGCACCACGTCCCAAACAT 1800
     -------+---------+---------+---------+---------+
     GAGTAGTCGGACAGGCTCCTCGCGTAGTCACGCGTGGTGCAGGGTTTGTA
      L  I  S  L  S  E  E  R  I  S  A  H  H  V  P  N  M

1801 GGTGGCCACCGAATGCGGCTGCCGGTGACCTCGCGCCGTGCTCCTCGTGC 1850
     -------+---------+---------+---------+---------+
     CCACCGGTGGCTTACGCCGACGGCCACTGGAGCGCGGCACGAGGAGCACG
      V  A  T  E  C  G  C  R

1851 TGCCCCGGCCCGTATTTATTCGGACCCCGTCATTGCCCCATTAAACACGG 1900
     -------+---------+---------+---------+---------+
     ACGGGGCCGGGCATAAATAAGCCTGGGGCAGTAACGGGGTAATTTGTGCC

1901 GAAGGC 1906
     -----
     CTTCCG
```

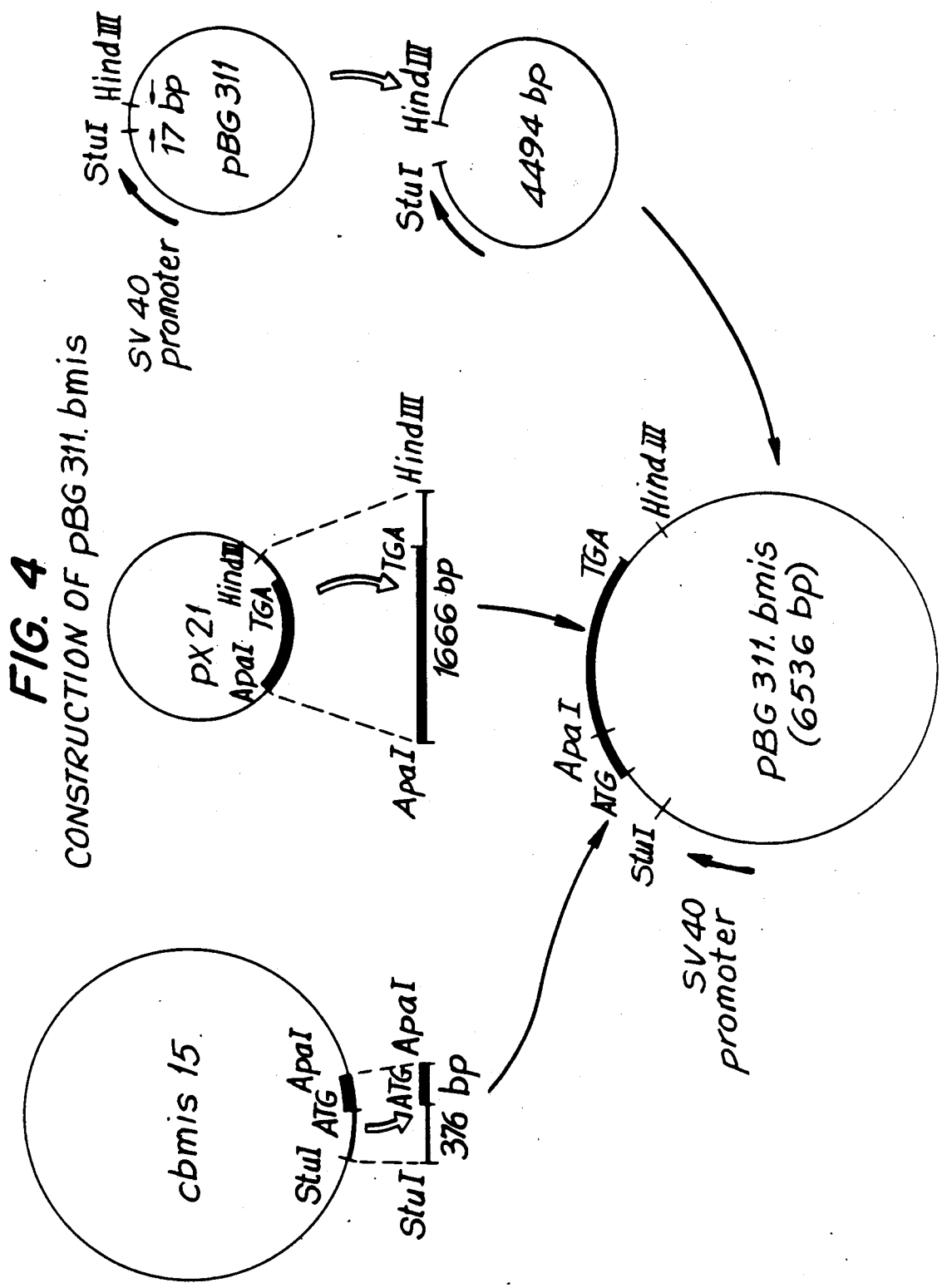

FIG. 6A  DNA SEQUENCE OF HUMAN MIS GENE

```
    AAGGTCGCGGCAGAGGAGATAGGGGTCTGTCCTGCACAAACACCCCACCT      50
  1 -------+---------+---------+---------+---------+
    TTCCAGCGCCGTCTCCTCTATCCCCAGACAGGACGTGTTTGTGGGGTGGA

TCCACTCGGCTCACTTAAGGCAGGCAGCCCAGCCCCTGGCAGCACCCACG     100
 51 -------+---------+---------+---------+---------+
    AGGTGAGCCGAGTGAATTCCGTCCGTCGGGTGGGGACCGTCGTGGGTGC

ATGCGGGACCTGCCTCTCACCAGCCTGGCCCTAGTGCTGTCTGCCCTGGG    150
101 -------+---------+---------+---------+---------+
    TACGCCCTGGACGGAGAGTGGTCGGACCGGGATCACGACAGACGGGACCC
    M   R   D   L   P   L   T   S   L   A   L   V   L   S   A   L   G

GGCTCTGCTGGGGACTGAGGCCCTCAGAGCAGAGGAGCCAGCTGTGGGCA    200
151 -------+---------+---------+---------+---------+
    CCGAGACGACCCCTGACTCCGGGAGTCTCGTCTCCTCGGTCGACACCCGT
    A   L   L   G   T   E   A   L   R   A   E   E   P   A   V   G   T

CCAGTGGCCTCATCTTCCGAGAAGACTTGGACTGGCCTCCAGGCATCCCA    250
201 -------+---------+---------+---------+---------+
    GGTCACCGGAGTAGAAGGCTCTTCTGAACCTGACCGGAGGTCCGTAGGGT
    S   G   L   I   F   R   E   D   L   D   W   P   P   G   I   P
```

```
      CAAGAGCCTCTGTGCCTGGTGGCACTGGGGGGAGACAGCAATGGCAGCAG
251   --------+---------+---------+---------+---------+ 300
      GTTCTCGGAGACACGGACCACCGTGACCCCCGCCTGTCGTTACCGTCGTC

Q  E  P  L  C  L  V  A  L  G  G  D  S  N  G  S  S

CTCCCCCTGCGGGTGGTGGGGGCTCTAAGGCGCCTATGAGCAGGCCTTCC
301   --------+---------+---------+---------+---------+ 350
      GAGGGGGACGCCCACCACCCCCGAGATTCGGGATACTCGTCCGGAAGG

S  P  L  R  V  V  G  A  L  S  A  V  E  Q  A  F  L

TGGGGGCCGTGCAGAGGGCCCGCTGGGGCCCCGAGACCTGGCCACCTTC
351   --------+---------+---------+---------+---------+ 400
      ACCCCCGGCACGTCTCCCGGGCGACCCCGGGGCTCTGGACCGGTGGAAG

G  A  V  Q  R  A  R  W  G  P  R  D  L  A  T  F

GGGGTCTGCAACACCGGTGACAGGCAGGCTGCCTTGCCCTCTCTACGGCG
401   --------+---------+---------+---------+---------+ 450
      CCCCAGACGTTGTGGCCACTGTCCGTCCGACGGAACGGGAGAGATGCCGC

G  V  C  N  T  G  D  R  Q  A  A  L  P  S  L  R  R

GCTGGGGCCTGCTGCGGGACCCTGGGGGCAGCGCCTGGTGGTCCTAC
451   --------+---------+---------+---------+---------+ 500
      CGACCCCGGACGACGCCCTGGGAGCCCCCGTCGCGGACCACCAGGATG

```
     ACCTGGAGGAAGGTATGTGGGCCCCAGCCCCCAAGCTTGGCACCGCCGTCT
501  --------+---------+---------+---------+---------+ 550
     TGGACCTCCTTCCATACACCCGGGGTCGAACCGTGGCGGCAGA
                L  E  E

TCCTTCAGGTGGGCCGGGTCCTCCTAGGGAAGATCAGGGGCTGGCAGAGC
551  --------+---------+---------+---------+---------+ 600
     AGGAAGTCCACCCGGCCCAGGAGGATCCCTTCTAGTCCCCGACCGTCTCG

CCCCACCCCTGGGCCAGGAGGCTGTGGTCTTGTTCCTAGGACTGGGTTGCG
601  --------+---------+---------+---------+---------+ 650
     GGGGTGGGACCCGTCCCTCCGACACCAGAACAAGGATCCTGACCCAACGC

GGTCCGTGGCCTGGAAGGTGGGCACCACACTCTGTCCTGTCCCCGAAGCC
651  --------+---------+---------+---------+---------+ 700
     CCAGGCACCGGACCTTCCACCCGTGGTGTGAGACAGGACAGGGGCTTCGG

CAGCTCTCTTAGACTTGCCCCTGCCTGCCAGGGAGGAGAGCTGCTGCCT
701  --------+---------+---------+---------+---------+ 750
     GTCGAGAATCTGAACGGGACGGAGCCACGTCCCTCTCTCGACGACGGA
```

FIG. 6D

```
     TCTCCCCACCCCTGAAGAGACGCAGGGCTCGGGGCCAGTGGAACCCTTC
751  -------+---------+---------+---------+---------+ 800
     AGAGGGGTGGGGACTTCTGCTGCGTCCCGAGCCCGGTCACCTTGGAAG

TTCCCACAGCCCCAGCCTGTTCTCAGGGCGCTGGCCTAAGATACTCCCT
801  -------+---------+---------+---------+---------+ 850
     AAGGGTGTCGGGGTCGGACAAGAGTCCCGGCGACCGGATTCTATGAGGGA

GCGGGGAAGGGGCTTCATCGGGCACCCCAACCCCAGAGACCCCAGGGCGGC
851  -------+---------+---------+---------+---------+ 900
     CGCCCCTTCCCCGAAGTAGCCCGTGGGGTTGGGGTCTCTGGGGTCCCGCCG

AGCCCCACCCACAGCCTCAGACGCAGCCCCTGCCTGCCCCTGCCGTCACC
901  -------+---------+---------+---------+---------+ 950
     TCGGGGTGGGTGTCGGAGTCTGCGTCGGGGACGACGGGACGGCAGTGG

GCTCCCTGGCTGCAGGAAGGCAGCTAAGAGGGGCACCCTTGTCCCCGCT
951  -------+---------+---------+---------+---------+ 1000
     CGAGGGACCGACGTCCTTCCGTCGATTCTCCCCGTGGGAACAGGGGGCGA
```

FIG. 6E

```
1001  TGAGGTCCCCTGCACAGTGGCCAGAGCGGCCAGGACAGATT
      ----------+---------+---------+---------+ 1050
      ACTCCAGGGGACGTGTCACCGGTCTCGCCGGTCCCTGTCTAGGGTTTCTAA

1051  CCCGGGGGGTGTGGCCCTTCAATGGCTCAGGCGTCCCCTGCTGTCCCGGCT
      ----------+---------+---------+---------+ 1100
      GGGCCCCCCACACCGGGAAGTTACCGAGTCCGCAGGGACGACAGGGCCGA

1101  GCAGTGACCTGGGAGCCAACACCCTCGCTGAGGTTCCAGGAGCCCCCGCC
      ----------+---------+---------+---------+ 1150
      CGTCACTGGACCCTCGGTTGTGGGAGCGACTCCAAGGTCCTCGGGGGCGG
        V  T  W  E  P  T  P  S  L  R  F  Q  E  P  P  P

1151  TGGAGGAGCTGGCCCCCCAGAGCTGGCCTGCTGGTCGTGTACCCTGGGC
      ----------+---------+---------+---------+ 1200
      ACCTCCTCGACCGGGGGGTCTCGACCGGACGACCAGCACATGGGACCCG
        G  G  A  G  P  P  E  L  A  L  L  V  L  V  P  G  P

1201  CTGGCCCTGAGGTCACTGTGACGAGGGCTGGGGCTGCCGGGTGCCCAGGTA
      ----------+---------+---------+---------+ 1250
      GACCGGGACTCCAGTGACACTGCTCCCGACGAGGCCCACGGGTCCAT
        G  P  E  V  T  V  T  R  A  G  L  P  G  A  Q
```

FIG. 6F

```
      CCAGGGAGTTGCATGGGGCAGTGCCCGGGCCCGTGGGCGGGGGCATGAATT
1251  -------+---------+---------+---------+---------+ 1300
      GGTCCCTCAACGTACCCCGTCACGGGCCCGGGCACCCGCCCCCGTACTTAA

TGTTGCAGGGTCTGCAGTACTGAGAACAGCGTAGAACCAGTGGGCGATGGG
1301  -------+---------+---------+---------+---------+ 1350
      ACAACGTCCCAGACGTCATGACTCTTGTCGCATCTTGGTCACCGCTACCC

AGGAAGGGGACCGGTAGAGAGCCTGGGTAAGCCTCCATCCAGCCGGGGC
1351  -------+---------+---------+---------+---------+ 1400
      TCCTTCCCCTGGCCATCTCGCCCGACCCATTCGGAGGTAGGTCGGCCCG

TGAGCCCTGGTCTCCGCAGAGCCTCTGCCCCTCCCGAGACACCCGCTACC
1401  -------+---------+---------+---------+---------+ 1450
      ACTCGGGACCAGAGGGGTCTCGGAGAGGGCTCTGTGGGCGATGG

TGGTGTTAGCGGTGGACCGCCCTGCGGGCCTGGGCCTCCGGGCTG
1451  -------+---------+---------+---------+---------+ 1500
      ACCACAATCGCCACCTGGCGGGACCCCGGACCGGAGCCCGAC

```
     GCCTTGACCCCTGCAGCCCCGCGGAGAGGGTAGGTCCGCGTGGAGAGGGAC
1501 --------+---------+---------+---------+---------+ 1550
     CGGAACTGGGACGTCGGGGCGCCTCTCCCATCCAGGCGCACCTCTCCCTG

A  L  T  L  Q  P  R  G  E

GGGGAGCCGGGTCGACTGCCCCCCGGGCCCCCAGCCCCTGAGCCAGCCGCG
1551 --------+---------+---------+---------+---------+ 1600
     CCCCTCGGCCCAGCTGACGGGGGGCCCGGGGGTCGGGGACTCGGTCGGCGC

TGCCCACCCACCGCAGACTCCCGGCTGAGTACCGCCCGGCTGCAGGCACT
1601 --------+---------+---------+---------+---------+ 1650
     ACGGGTGGGTGGCGTCTGAGGGCCGACTCATGGCGGGCCGACGTCCGTGA

D  S  R  L  S  T  A  R  L  Q  A  L

GCTGTTCGGCGACGACCACCGCTGCTTCACACGGATGACCCCGGCCCTGC
1651 --------+---------+---------+---------+---------+ 1700
     CGACAAGCCGCTGCTGGTGGCGACGAAGTGTGCCTACTGGGGCCGGGACG

L  F  G  D  D  H  R  C  F  T  R  M  T  P  A  L  L

TCCTGCTGCCGGGTTCGGAGCCCGCTGCCGGCACGGCCAGCTG
1701 --------+---------+---------+---------+---------+ 1750
     AGGACGACGGCCCAGGCCTCGGGCGACGGCCGTGCCGGTCGAC

```
      GACACCGTGCCCTTCCCGCCGCCCAGGTGCGGCAGGCACCGGGACACGG
1751  ------------+---------+---------+---------+---------+  1800
      CTGTGGCACGGGAAGGGCGGCGGGTCCACGCCGTCCGTGGCCCTGTGCC

D  T  V  P  F  P  P  R

GGCAGGAGCGGGCGGGGCGGCGGTGGCCTCGTGGCCGCTCTCAACTCCTC
1801  ------------+---------+---------+---------+---------+  1850
      CCGTCCTCGCCCGCCCCCGCCGCCACCGGAGCACCGGCGAGAGTTGAGGAG

P  S  A  E  L  E  E  S  P  P  S

CAATTGCGGGTTCCAGGCCATCCGGGAACTCGAGGAGTCGCCACCCAGC
1851  ------------+---------+---------+---------+---------+  1900
      GTTAACGCCCAAGGTCCGGTAGGCCTTGAGCTCCTCAGCGGTGGGTCG

P  S  A  E  L  E  E  S  P  P  S

GCAGACCCCCTTCCTGGAGACGCTGACGCGGCTGGTTGCGGGGCTGCGGGT
1901  ------------+---------+---------+---------+---------+  1950
      CGTCTGGGGAAGGACCTCTGCGAGTGCGCCGACCACGCCCGACGCCCA

A  D  P  F  L  E  T  L  T  R  L  V  R  A  L  R  V

CCCCCCGGCCCGGCCTCCGCGCCCCGGCGCCCTGGATCCGGACGCGC
1951  ------------+---------+---------+---------+---------+  2000
      GGGGGGCCGGGCCGGAGGCGCGGGCCGCGGGACCTAGGCCTGCGCG

```
      TGGCCGGCTTCCCGCAGGGCCTAGTCAACCTGTCGGACCCCGCGGCTG
2001  ------------------------------------------------  2050
      ACCGGCCGAAGGGCGTCCCGGATCAGTTGGACAGCCTGGGGCCGCGAC
       A  G  F  P  Q  G  L  V  N  L  S  D  P  A  A  L

GAGCGCCTACTCGACGGGGAGGAGCCGCTGCTGCTGCTGAGGCCCAC
2051  ------------------------------------------------  2100
      CTCGCGGATGAGCTGCCCCTCCTCGGCGACGACGACGACTCCGGGTG
       E  R  L  L  D  G  E  E  P  L  L  L  L  R  P  T

TGCGGCCACCACCGGGGATCCTGCGCCCCTGCACGACCCACGTCGGCGC
2101  ------------------------------------------------  2150
      ACGCCGGTGGTGGCCCCTAGGACGCGGGGACGTGCTGGGTGCAGCCGCG
       A  A  I  T  G  D  P  A  P  L  H  D  P  T  S  A  P

CGTGGGCCACGGCCCTGGCCGCGCGCCGGTGCTGCTGAACTGCAAGCGGCG
2151  ------------------------------------------------  2200
      GCACCCGGTGCCGGGACCGGCGCGCGGCCACGACTTGACGTTCGCCGC
       W  A  T  A  L  A  R  R  V  A  A  E  L  Q  A  A

GCTGCCGAGCTGCGAAGCCTCCGGGTCTGCCTCCGGCCACAGCCCCGCT
2201  ------------------------------------------------  2250
      CGACGGCTCGACGCTTCGGAGGCCCAGAGACGGAGGCCGGTGTCGGGGCGA
       A  A  E  L  R  S  L  P  G  L  P  P  A  T  A  P  L
```

FIG. 6J

```
2251 GCTGGGCGGCCTGTCTCGCGGCTCTGCCCAGGAGGCCCCGGGGCCTCGGCG 2300
     -----+----+----+----+----+----+----+----+----+----+
     CGACCCGCCGGACAGAGCGCCGAGACGGGTCCTCCGGGGCCCCGGAGCCGC
      L  A  R  L  L  A  L  C  P  G  G  P  G  G  L  G  D

2301 ATCCCCTGCGAGGCGCTGCTGCTCCTGAAGGCGCTGCAGGGCCTGCGCGTG 2350
     -----+----+----+----+----+----+----+----+----+----+
     TAGGGGACGCTCGCGACGACGAGGACTTCCGCGACGTCCCGGACGCGCAC
      P  L  R  A  L  L  L  L  K  A  L  Q  G  L  R  V

2351 GAGTGGCGCGGGGATCCGCGGGGCCCGGGTCGGGCACAGCGGCAGCGC 2400
     -----+----+----+----+----+----+----+----+----+----+
     CTCACCGCGCCCCTAGGCGCCCCGGGCCCAGCCCGTGTCGCCGTCGCG
      E  W  R  G  R  D  P  R  G  P  G  R  A  Q  R  S  A

2401 GGGGGCCACCGCCGCGACGGGCCGTGCGCGCTGCGCGAGCTCAGCGTAG 2450
     -----+----+----+----+----+----+----+----+----+----+
     CCCCCGGTGGGCGGCGCTGCCCGGCACGCGCGACGCGCTCGAGTCGCATC
      G  A  T  A  A  D  G  P  C  A  L  R  E  L  S  V  D

2451 ACCTCCGCGCCGAGCGCTCCGTACTCATCCCCGAGACCTACCAGGCCAAC 2500
     -----+----+----+----+----+----+----+----+----+----+
     TGGAGGCGCGGCTCGCGAGGCATGAGTAGGGGCTCTGGATGGTCCGGTTG
      L  R  A  E  R  S  V  L  I  P  E  T  Y  Q  A  N

2501 AATTGCCAGGGCGTGTGCGGCTGGCCTCAGTCCGACCGCAACCCGCGCTA 2551
     -----+----+----+----+----+----+----+----+----+----+
     TTAACGGTCCCGCACACGCCGACCGGAGTCAGGCTGGCGTTGGGCGCGAT
      N  C  Q  G  V  C  G  W  P  Q  S  D  R  N  P  R  Y
```

FIG. 6K

```
2551 CGGCAACCACGTGGTGCTGCTGAAGATGCAGGCCCGTGGGCCGCCC
     ----+----+----+----+----+----+----+----+----+----+ 2600
     GCCGTTGGTGCACCACGACGACTTCTACGTCCGGGCACCCGGCGGG
      G   N   H   V   V   L   L   K   M   Q   A   R   G   A   A   L

2601 TGGGCGCGCCCACCCTGCTGCGTGCCCACCGCCTACGCGGGCAAGCTGCTC
     ----+----+----+----+----+----+----+----+----+----+ 2650
     ACCGCGCGGGTGGGACGACGACGCACGGGTGGCGGATGCGCCCGTTCGACGAG
      A   R   P   P   C   C   V   P   T   A   Y   A   G   K   L   L

2651 ATCAGCCTGTCGGAGGAACGCATCAGCGCGCACCACGTGCCCAACATGGT
     ----+----+----+----+----+----+----+----+----+----+ 2700
     TAGTCGGACAGCCTCCTTGCGTAGTCGCGCGTGGTGCACGGGTTGTACCA
      I   S   L   S   E   E   R   I   S   A   H   H   V   P   N   M   V

2701 GGCCACCGAGTGTGGCTGCCGGTGACCCCTGCCGCCGGACTCCTGCC
     ----+----+----+----+----+----+----+----+----+----+ 2750
     CCGGTGGCTCACACCGACGGCCACTGGGGACGGCGGCCTGAGGACGG
      A   T   E   C   G   C   R

2751 CCGAGGGTCCGGACGCGCCCCAGCTCGCGCCCCTTCCCATATTATTCGG
     ----+----+----+----+----+----+----+----+----+----+ 2800
     GGCTCCCAGGCCTGCGCGGGGTCGAGCGCGGGAAGGGTATAATAAGCC

2801 ACCCCAAGCATCGCCCCAATAAAGACCAGCAAGC
     ----+----+----+----+----+----+----- 2834
     TGGGGTTCGTAGCGGGGTTATTTCTGGTCGTTCG
```

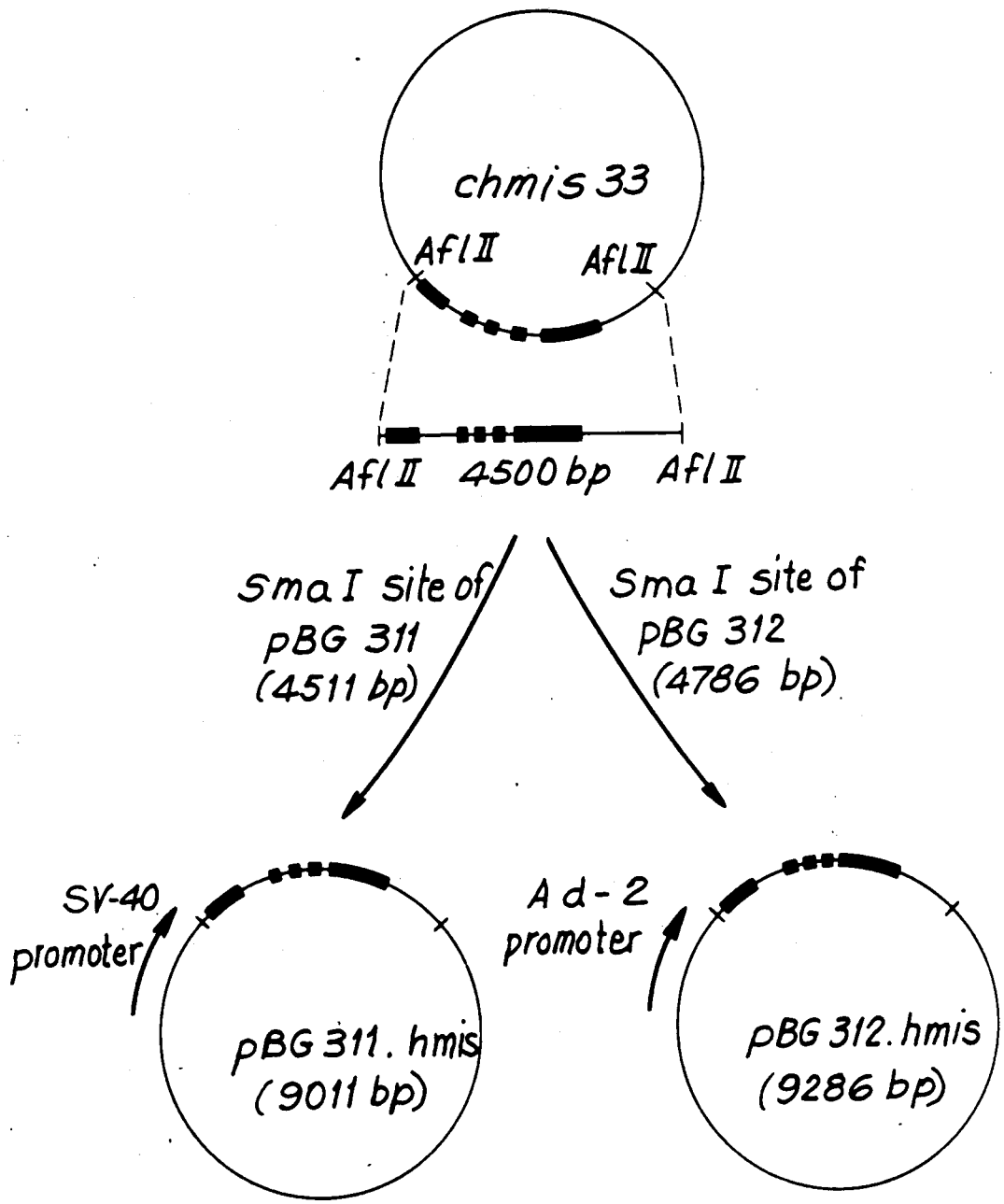

DNA SEQUENCES, RECOMBINANT DNA MOLECULES AND PROCESSES FOR PRODUCING MULLERIAN INHIBITING SUBSTANCE-LIKE POLYPEPTIDES

This invention relates to DNA sequences, recombinant DNA molecules and processes for producing Mullerian Inhibiting Substance (MIS)-like polypeptides. More particularly, the invention relates to DNA sequences and recombinant DNA molecules that are characterized in that they code for at least one MIS-like polypeptide. Accordingly, hosts transformed with these sequences may be employed in the processes of this invention to produce the MIS-like polypeptides of this invention. These polypeptides possess antitumor activity and are useful in the treatment of cancer, especially cancer of the female genital tract (e.g., ovarian cancer).

The production of at least two testicular factors by the male gonad shortly after differentiation was first postulated to be necessary for normal male reproductive development following the fetal rabbit castration experiments of Jost (*C. R. Soc. Biol.*, 140, 463-64 (1946) and *C. R. Soc. Biol.*, 141, 135-36 (1947)). One factor, testosterone, was shown to be responsible for differentiation of the epididymis, vas deferens, and seminal vesicles from the Wolffian ducts. Virilization of the male was not complete, however, unless a second, nonsteroidal, factor was present to stimulate regression of the Mullerian ducts, the anlagen of the female reproductive system. Jost later named this second regulatory factor Mullerian Inhibiting Substance (MIS) (*Rec. Prog. Horm Res.*, 8, 379-418 (1953)). Interest in purifying MIS was heightened by the finding that bovine MIS in addition to its important role in development, was cytotoxic to the human ovarian tumor cell line HOC-21 both in vitro (Donahoe et al., Science 205, 913-15 (1979); and Fuller et al., *J. Clin. Endocrinol. Metab.*, 54. 1051-55 (1982)) and in vivo in a nude mouse model (Donahoe et al., *Ann. Surg.*, 194, 472-80 (1981)). Highly purified fractions of bovine MIS also inhibit colony growth of primary ovarian and endometrial cancers derived from patients (Fuller et al., *Gyn. Oncol.* (1985)).

A variety of approaches have been used to attempt the purification of MIS (for reviews see Josso et al. *Rec. Prog. Hom. Res.*, 33, 117-67 (1977) and Donahoe et al., *Rec. Prog. Hom. Res.*, 38, 279-330 (1982)). Newborn calf testes contain a high level of MIS up to 8 weeks after birth (Donahoe et al., *Biol. Reprod.*, 16, 238-43 (1977)), providing an accessible tissue source for biochemical purification. Donahoe and coworkers originally obtained active, crude MIS preparations of calf testes by incubation with guanidine hydrochloride in the presence of a protease inhibitor (Swann et al., *Dev. Biol.*, 69, 73-84 (1979)). Subsequent fractionation by ion exchange or gel filtration chromatography enhanced purity about thirty-fold. Similar results were obtained by others working with incubation medium from fetal calf testes (Picard et al., *Biomedicine* 25, 147-50 (1976), and Josso et al. *Rec. Prog. Hom. Res.*, 33, 117-67 (1977)). The purity of bovine MIS was further enhanced when sequential ion exchange chromatography was coupled with sequential lectin affinity chromatography (Budzik et al., *Cell* 21, 909-15 (1980); U.S. Pat. No. 4,404,188; and U.S. Pat. No. 4,510,131). The results of Budzik et al. (supra) suggested that bovine MIS was a large molecular weight glycoprotein and provided semipurified MIS fractions that were used to prepare anti-MIS monoclonal antibodies (Mudgett-Hunter et al., *J. Immunol.*, 128, 1327-33 (1982); Shima et al., *Hybridoma*, 3, 201-14 (1984); and U.S. Pat. No. 4,487,833). Lectin-affinity-purified bovine MIS fractionated by gel filtration under native conditions exhibited a single peak at approximately 200,000 daltons, although on denaturing polyacrylamide gels, this fraction contained multiple components suggesting a multiple subunit structure (Budzik et al., *Cell*, 21, 909-15 (1980)).

Subsequently, Matrix Gel Green A was used to achieve greater than 2000-fold purification of bovine MIS with a concomitant 60% recovery of starting activity. This was achieved by stabilizing MIS activity with the dialyzable protecting agents 2-mercaptoethanol, EDTA, and Nonidet-P40 (NP40). Analysis of the 2000-fold-purified MIS fraction by SDS-polyacrylamide gel electrophoresis indicated that only one component, migrating at 140,000 daltons was sensitive to reduction, although a number of other moieties were detected. Reduction of the sample prior to electrophoresis showed a new band at 74,000 daltons with the simultaneous loss of the 140,000 dalton species, while the migrations of all other components in this fraction were effectively unchanged (Budzik et al., *Cell*, 34, 307-14 (1983)). This is consistent with the suggestion that bovine MIS is a dimer of disulfide-linked subunits with a total molecular weight of 124,000 daltons (Picard et al., *Mol. Cell. Endocrinol.*, 12, 17-30 (1978)).

MIS of greater purity and in large amounts is urgently needed for oncological studies because the present methods of treating cancers of the female genital tract are not adequate. Cancers of the female genital tract represent approximately 9 percent of all cancers in humans. Currently, physicians use surgery and radiation when genital tract cancers are detected in early stages (for example, ovarian carcinoma Stage I-IIa). Although these methods of treatment are effective, they render the patients sterile. Chemotherapy is used in advanced cases (Stage III-IV) when patients are classified as inoperable. Of the chemotherapeutic agents, cisplatinum, adriamycin and cytoxan are the most commonly used. These drugs have proven to be most effective when combined in cisplatinum containing regimens and used on a long-term basis. Each of these drugs is considered to be highly toxic and their use requires intermittent hospitalization of the patients.

MIS, as a natural biological regressor, is expected to have less side effects because of its specificity. Other potential uses of MIS include the treatment of tumors with high levels of epithelial growth factor (EGF) receptors (Hutson et al., *Science*, 223, 586-89 (1984)), such as those from the head and neck, lung, epithelial lining of the digestive tract, cornea and skin. It is also believed that MIS may inhibit germ cell meiosis since the substance has been localized to the granulosa cell of the Graffian follicle. Thus, its use as a contraceptive agent is being explored. These broader potential applications further increase the importance of providing an adequate source of MIS.

A purification procedure for bovine MIS has been devised by Donahoe and co-workers (Budzik et al., in *Developmental Mechanisms: Normal and Abnormal*, Lash, J. W., ed. Alan R. Liss, Inc., Scientific, Medical and Scholarly Publications, pages 207-23 (1985)). Using a scaled-up procedure, about 1 mg of 80% pure protein can be isolated from 1000 newborn calf testes. However, this purification process is labor intensive and costly. Most importantly, it does not provide enough material for extensive oncological studies. Recombinant DNA technology would provide a larger source of bovine MIS.

Although most work on MIS has been done on bovine MIS, there is also some interest in chick MIS. It appears from an article in *Chemical Week* (Jan. 30, 1985, page 69), that C. S. Teng claims to have purified chick MIS and isolated the MIS gene from chick embryos. However, no further details were reported.

For clinical use, human MIS is preferred to MIS of animal origin. Human MIS, however, is even more difficult to obtain because human tissue in sufficient quantities is not available; thus, the only way to produce human MIS is through recombinant DNA technology. Accordingly, the isolation of the human gene for MIS was of paramount importance.

The present invention addresses the foregoing problems by providing DNA sequences coding for at least one MIS-like polypeptide, recombinant DNA molecules comprising such sequences, hosts comprising such sequences and processes for producing such polypeptides in hosts transformed with those DNA sequences, and in higher purity than heretofore available.

The DNA sequences of this invention are selected from the group consisting of (a) the DNA sequences

```
AAGGTCGCGGCAGAGGAGATAGGGGTCTGTCCTGCACAAACACCCCACCT
TCCACTCGGCTCACTTAAGGCAGGCAGCCCAGCCCCTGGCAGCACCCACG
ATGCGGGACCTGCCTCTCACCAGCCTGGCCCTAGTGCTGTCTGCCCTGGG
GGCTCTGCTGGGGACTGAGGCCCTCAGAGCAGAGGAGCCAGCTGTGGGCA
CCAGTGGCCTCATCTTCCGAGAAGACTTGGACTGGCCTCCAGGCATCCCA
CAAGAGCCTCTGTGCCTGGTGGCACTGGGCGGGGACAGCAATGGCAGCAG
CTCCCCCCTGCGGGTGGTGGGGGCTCTAAGCGCCTATGAGCAGGCCTTCC
TGGGGGCCGTGCAGAGGGCCCGCTGGGGCCCCCGAGACCTGGCCACCTTC
GGGGTCTGCAACACCGGTGACAGGCAGGCTGCCTTGCCCTCTCTACGGCG
GCTGGGGGCCTGGCTGCGGGACCCTGGGGGGCAGCGCCTGGTGGTCCTAC
ACCTGGAGGAAGGTATGTGGGGCCCAGCCCCAAGCTTGGCACCGCCGTCT
TCCTTCAGGTGGGCCGGGTCCTCCTAGGGAAGATCAGGGGCTGGCAGAGC
CCCCACCCTGGGCAGGGAGGCTGTGGTCTTGTTCCTAGGACTGGGTTGCG
GGTCCGTGGCCTGGAAGGTGGGCACCACACTCTGTCCTGTCCCCGAAGCC
CAGCTCTTAGACTTGCCCCTGCCTCGGTGCCAGGGAGAGAGCTGCTGCCT
TCTCCCCACCCCTGAAGACGACGCAGGGCTCGGGGCCAGTGGAACCCTTC
TTCCCACAGCCCCAGCCTGTTCTCAGGGCCGCTGGCCTAAGATACTCCCT
GCGGGGAAGGGGCTTCATCGGGCACCCCAACCCAGAGACCCCAGGGCGGC
AGCCCCACCCACAGCCTCAGACGCAGCCCCTGCCTGCCCCTGCCGTCACC
GCTCCCTGGCTGCAGGAAGGCAGCTAAGAGGGGCACCCTTGTCCCCCGCT
TGAGGTCCCCTGCACAGTGGCCAGAGCGGCAGGGACAGATCCCAAAGATT
CCCGGGGGGTGTGGCCTTCAATGGCTCAGGCGTCCCCTGCTGTCCCGGCT
GCAGTGACCTGGGAGCCAACACCCTCGCTGAGGTTCCAGGAGCCCCCGCC
TGGAGGAGCTGGCCCCCCAGAGCTGGCGCTGCTGGTGCTGTACCCTGGGC
CTGGCCCTGAGGTCACTGTGACGAGGGCTGGGCTGCCGGGTGCCCAGGTA
CCAGGGAGTTGCATGGGGCAGTGCCCGGGCCGTGGCGGGGGGCATGAATT
TGTTGCAGGGTCTGCAGTACTGAGAACAGCGTAGAACCAGTGGCGATGGG
AGGAAGGGGACCGGTAGA3CGGGGCTGGGTAAGCCTCCATCCAGCCGGGC
TGAGCCCTGGTCTCCGCAGAGCCTCTGCCCCTCCCGAGACACCCGCTACC
TGGTGTTAGCGGTGGACCGCCCTGCGGGGGCCTGGCGCGGCTCCGGGCTG
GCCTTGACCCTGCAGCCCCGCGGAGAGGGTAGGTCCGCGTGGAGAGGGAC
GGGGAGCCGGGTCGACTGCCCCCGGGCCCCCAGCCCCTGAGCCAGCCGCG
TGCCCACCCACCGCAGACTCCCGGCTGAGTACCGCCCGGCTGCAGGCACT
GCTGTTCGGCGACGACCACCGCTGCTTCACACGGATGACCCCGGCCCTGC
TCCTGCTGCCGCGGTCCGAGCCCGCGCCGCTGCCTGCGCACGGCCAGCTG
GACACCGTGCCCTTCCCGCCGCCCAGGTGCGCGCAGGCACCGGGACACGG
GGCAGGAGCGGGCGGGGGCGGCGTGGCCTCGTGGCCGCTCTCAACTCCTC
CAATTGCGGGTTCCAGGCCATCCGCGGAACTCGAGGAGTCGCCACCCAGC
GCAGACCCCTTCCTGGAGACGCTCACGCGCCTGGTGCGGGCGCTGCGGGT
CCCCCCGGCCCGGGCCTCCGCGCCGCGCCTGGCCCTGGATCCGGACGCGC
TGGCCGGCTTCCCGCAGGGCCTAGTCAACCTGTCGGACCCCGCGGCGCTG
GAGCGCCTACTCGACGGCGAGGAGCCGCTGCTGCTGCTGAGGCCCAC
TGCGGCCACCACCGGGGATCCTGCGCCCCTGCACGACCCCACGTCGGCGC
CGTGGGCCACGGCCCTGGCGCGCCGCGTGGCTGCTGAACTGCAAGCGGCG
GCTGCCGAGCTGCGAAGCCTCCCGGGTCTGCCTCCGGCCACAGCCCCGCT
GCTGGCGCGCCTGCTCGCGCTCTGCCCAGGAGGCCCCGGCGGCCTCGGCG
ATCCCCTGCGAGCGCTGCTGCTCCTGAAGGCGCTGCAGGGCCTGCGCGTG
GAGTGGCGCGGGCGGGATCCGCGCGGGCCGGGTCGGGCACAGCGCAGCGC
GGGGGCCACCGCCGCCGACGGGCCGTGCGCGCTGCGCGAGCTCAGCGTAG
ACCTCCGCGCCGAGCGCTCCGTACTCATCCCCGAGACCTACCAGGCCAAC
AATTGCCAGGGCGTGTGCGGCTGGCCTCAGTCCGACCGCAACCCGCGCTA
CGGCAACCACGTGGTGCTGCTGCTGAAGATGCAGGCCCGTGGGGCCGCCC
TGGCGCGCCCACCCTGCTGCGTGCCCACCGCCTACGCGGGCAAGCTGCTC
ATCAGCCTGTCGGAGGAACGCATCAGCGCGCACCACGTGCCCAACATGGT
GGCCACCGAGTGTGGCTGCCGGTGACCCCTGCGCCGCGCGGACTCCTGCC
CCGAGGGTCCGGACGCGCCCCAGCTCGCGCCCCTTCCCATATTTATTCGG
ACCCCAAGCATCGCCCCAATAAAGACCAGCAAGC
```

(the sequence of the human gene);

```
AGCACCCACGATGCGGGACCTGCCTCTCACCAGCCTGGCCCTAGTGCTGT
CTGCCCTGGGGGCTCTGCTGGGGACTGAGGCCCTCAGAGCAGAGGAGCCA
GCTGTGGGCACCAGTGGCCTCATCTTCCGAGAAGACTTGGACTGGCCTCC
AGGCATCCCACAAGAGCCTCTGTGCCTGGTGGCACTGGGCGGGGACAGCA
ATGGCAGCAGCTCCCCCCTGCGGGTGGTGGGGGCTCTAAGCGCCTATGAG
CAGGCCTTCCTGGGGGCCGTGCAGAGGGCCCGCTGGGGCCCCCGAGACCT
GGCCACCTTCGGGGTCTGCAACACCGGTGACAGGCAGGCTGCCTTGCCCT
CTCTACGGCGGCTGGGGGCCTGGCTGCGGGACCCTGGGGGGCAGCGCCTG
GTGGTCCTACACCTGGAGGAAGTGACCTGGGAGCCAACACCCTCGCTGAG
```

-continued

```
GTTCCAGGAGCCCCCGCCTGGAGGAGCTGGCCCCCCAGAGCTGGCGCTGC
TGGTGCTGTACCCTGGGCCTGGCCCTGAGGTCACTGTGACGAGGGCTGGG
CTGCCGGGTGCCCAGAGCCTCTGCCCCTCCCGAGACACCCGCTACCTGGT
GTTAGCGGTGGACCGCCCTGCGGGGGCCTGGCGCGGCTCCGGGCTGGCCT
TGACCCTGCAGCCCCGCGGAGAGGACTCCCGGCTGAGTACCGCCCGGCTG
CAGGCACTGCTGTTCGGCGACGACCACCGCTGCTTCACACGGATGACCCC
GGCCCTGCTCCTGCTGCCGCGGTCCGAGCCCGCGCCGCTGCCTGCGCACG
GCCAGCTGGACACCGTGCCCTTCCCGCCGCCCAGGCCATCCGCGGAACTC
GAGGAGTCGCCACCCAGCGCAGACCCCTTCCTGGAGACGCTCACGCGCCT
GGTGCGGGCGCTGCGGGTCCCCCCGGCCCGGGCCTCCGCGCCGCGCCTGG
CCCTGGATCCGGACGCGCTGGCCGGCTTCCCGCAGGGCCTAGTCAACCTG
TCGGACCCCGCGGCGCTGGAGCGCCTACTCGACGGCGAGGAGCCGCTGCT
GCTGCTGCTGAGGCCCACTGCGGCCACCACCGGGGATCCTGCGCCCCTGC
ACGACCCCACGTCGGCGCCGTGGGCCACGGCCCTGGCGCGCCGCGTGGCT
GCTGAACTGCAAGCGGCGGCTGCCGAGCTGCGAAGCCTCCCGGGTCTGCC
TCCGGCCACAGCCCCGCTGCTGGCGCGCCTGCTCGCGCTCTGCCCAGGAG
GCCCCGGCGGCCTCGGCGATCCCCTGCGAGCGCTGCTGCTCCTGAAGGCG
CTGCAGGGCCTGCGCGTGGAGTGGCGCGGGCGGGATCCGCGCGGGCCGGG
TCGGGCACAGCGCAGCGCGGGGGCCACCGCCGCCGACGGGCCGTGCGCGC
TGCGCGAGCTCAGCGTAGACCTCCGCGCCGAGCGCTCCGTACTCATCCCC
GAGACCTACCAGGCCAACAATTGCCAGGGCGTGTGCGGCTGGCCTCAGTC
CGACCGCAACCCGCGCTACGGCAACCACGTGGTGCTGCTGCTGAAGATGC
AGGCCCGTGGGGCCGCCCTGGCGCGCCCACCCTGCTGCGTGCCCACCGCC
TACGCGGGCAAGCTGCTCATCAGCCTGTCGGAGGAACGCATCAGCGCGCA
CCACGTGCCCAACATGGTGGCCACCGAGTGTGGCTGCCGGTGACCCCTGC
GCCGCGCGGACTCCTGCCCCGAGGGTCCGGACGCGCCCCAGCTCGCGCCC
CTTCCCATATTTATTCGGACCCCAAGCATCGCCCCAATAAAGACCAGCAA
GC
```
(the sequence of human cDNA);
```
CAAGGTCATGTCCCAGGAGGAGATAGGGACCGCCCTGCACCACAAACAGC
TCTGCTCCCTCTTATAAAGTAGGGCAGCCCAGCCCCTGGAAGCTCCCAGG
ATGCCCGGTCCATCTCTCTCTCTGGCCCTGGTGCTGTCGGCCATGGGGGC
TCTGCTGAGGCCAGGGACCCCCAGGGAAGAAGTCTTCAGCACCTCAGCCT
TGCCCAGGGAGCAGGCCACAGGCAGCGGGGCACTCATCTTTCAGCAAGCC
TGGGACTGGCCACTCTCCAGTCTCTGGCTGCCAGGCAGCCCTCTGGACCC
CCTGTGCCTGGTGACCCTGCATGGGAGTGGCAACGGGAGCAGGGCCCCCC
TGCGGGTGGTGGGGGTCCTGAGCAGCTACGAGCAGGCCTTCCTGGAGGCT
GTGCGGCGCACCCACTGGGGCCTGAGTGACTTGACCACCTTCGCAGTGTG
CCCCGCTGGCAACGGGCAGCCTGTGCTGCCCCACCTGCAGCGGCTGCAGG
CATGGCTGGGGGAGCCCGGGGGGCGGTGGCTGGTGGTCCTGCACCTGGAG
GAAGTGACGTGGGAGCCAACACCCTTGCTGAGGTTCCAGGAGCCTCCGCC
TGGAGGAGCCAGCCCCCAGAGCTGGCGCTGCTGGTGGTGTACCCAGGGC
CTGGCCTGGAGGTCACTGTCACCGGGGCTGGGCTACCTGGCACCCAGAGC
CTCTGCCTGACCGCGGACTCGGACTTCCTGGCCTTGGTCGTGGACCACCC
GGAGGGGGCCTGGCGCCGGCCTGGGTTAGCCCTTACCCTGCGGCGCCGTG
GAAATGGTGCGCTCCTGAGCACTGCCCAGCTGCAGGCGCTGCTGTTCGGT
GCGGACTCCCGCTGCTTCACACGAAAGACCCCAGCCCTGTTACTCTTGCT
GCCGGCCCGGTCTTCGGCACCGATGCCCGCGCACGGTCGGCTGGACTTGG
TGCCCTTCCCGCAGCCCAGGGCTTCCCCGGAGCCAGAGGAGGCACCGCCC
AGCGCTGATCCCTTCCTGGAGACTCTCACGCGCCTGGTGCGCGCGCTTGC
GGGACCCCCGGCCCGAGCCTCGCCACCGCGGCTGGCCTTGGACCCGGGCG
CACTGGCTGGTTTCCCGCAGGGCCAGGTCAACCTGTCGGACCCCGCGGCC
CTGGAGCGCCTGCTGGACGGCGAGGAGCCGCTGCTGCTGCTGCTGCCGCC
GACGGCAGCCACCACCGGGGTCCCCGCAACGCCGCAAGGTCCCAAGTCCC
CTCTGTGGGCCGCGGGACTAGCGCGCCGGGTGGCTGCCGAGCTTCAGGCG
GTGGCCGCCGAGCTGCGTGCCCTCCCGGGGCTGCCTCCAGCTGCCCCACC
GCTGCTGGCGCGCCTGCTGGCACTGTGCCCGGGAAACCCAGACAGCCCCG
GCGGCCCGCTGCGCGCGCTGCTGCTGCTCAAAGCGCTGCAGGGCCTGCGC
GCTGAGTGGCGCGGGCGGGAGCGGAGCGGCTCTGCACGGGCGCAGCGCAG
CGCCGGGGCCGCGGCTGCAGACGGGCCGTGCGCTCTGCGTGAGCTGAGCG
TAGACCTGCGGGCCGAGCGCTCGGTGCTCATCCCCGAGACATACCAGGCC
AACAACTGCCAGGGGGCCTGCGGCTGGCCTCAGTCGGACCGCAACCCGCG
CTACGGCAACCACGTGGTGCTGCTGCTAAAGATGCAGGCCCGCGGCGCCA
CCCTGGCGCGCCCGCCCTGCTGTGTGCCCACAGCCTACACCGGCAAGCTC
CTCATCAGCCTGTCCGAGGAGCGCATCAGTGCGCACCACGTGCCCAAACAT
GGTGGCCACCGAATGCGGCTGCCGGTGACCTCGCGCCGTGCTCCTCGTGC
TGCCCCGGCCCGTATTTATTCGGACCCCGTCATTGCCCCATTAAACACGG
GAAGGC
```
(the sequence of the bovine gene); and
```
AGCTCCCAGGATGCCCGGTCCATCTCTCTTTCTGGCCCTGGTGCTGTCGG
CCATGGGGGCTCTGCTGAGGCCAGGGACCCCCAGGGAAGAAGTCTTCAGC
ACCTCAGCCTTGCCCAGGGAGCAGGCCACAGGCAGCGGGGCACTCATCTT
TCAGCAAGCCTGGGACTGGCCACTCTCCAGTCTCTGGCTGCCAGGCAGCC
CTCTGGACCCCCTGTGCCTGGTGACCCTGCATGGGAGTGGCAACGGGAGC
AGGGCCCCCCTGCGGGTGGTGGGGGTCCTGAGCAGCTACGAGCAGGCCTT
CCTGGAGGCTGTGCGGCGCACCCACTGGGGCCTGAGTGACTTGACCACCT
TCGCAGTGTGCCCCGCTGGCAACGGGCAGCCTGTGCTGCCCCACCTGCAG
CGGCTGCAGGCATGGCTGGGGGAGCCCGGGGGGCGGTGGCTGGTGGTCCT
GCACCTGGAGGAAGTGACGTGGGAGCCAACACCCTTGCTGAGGTTCCAGG
AGCCTCCGCCTGGAGGAGCCAGCCCCCAGAGCTGGCGCTGCTGGTGGTG
TACCCAGGGCCTGGCCTGGAGGTCACTGTCACCGGGGCTGGGCTACCTGG
CACCCAGAGCCTCTGCCTGACCGCGGACTCGGACTTCCTGGCCTTGGTCG
TGGACCACCCGGAGGGGGCCTGGCGCCGGCCTGGGTTAGCCCTTACCCTG
```

-continued

```
CGGCGCCGTGGAAATGGTGCGCTCCTGAGCACTGCCCAGCTGCAGGCGCT
GCTGTTCGGTGCGGACTCCCGCTGCTTCACACGAAAGACCCCAGCCCTGT
TACTCTTGCTGCCGGCCCGGTCTTCGGCACCGATGCCCGCGCACGGTCGG
CTGGACTTGGTGCCCTTCCCGCAGCCCAGGGCTTCCCCGGAGCCAGAGGA
GGCACCGCCCAGCGCTGATCCCTTCCTGGAGACTCTCACGCGCCTGGTGC
GCGCGCTTGCGGGACCCCCGGCCCGAGCCTCGCCACCGCGGCTGGCCTTG
GACCCGGGCGCACTGGCTGGTTTCCCGCAGGGCCAGGTCAACCTGTCGGA
CCCCGCGGCCCTGGAGCGCCTGCTGGACGGCGAGGAGCCGCTGCTGCTGC
TGCTGCCGCCGACGGCAGCCACCACCGGGGTCCCCGCAACGCCGCAAGGT
CCCAAGTCCCCTCTGTGGGCCGCGGGACTAGCGCGCCGGGTGGCTGCCGA
GCTTCAGGCGGTGGCCGCCGAGCTGCGTGCCCTCCCGGGGCTGCCTCCAG
CTGCCCCACCGCTGCTGGCGCGCCTGCTGGCACTGTGCCCGGGAAACCCA
GACAGCCCCGGCGGCCCGCTGCGCGCGCTGCTGCTGCTCAAAGCGCTGCA
GGGCCTGCGCGCTGAGTGGCGCGGGCGGGAGCGGAGCGGCTCTGCACGGG
CGCAGCGCAGCGCCGGGGCCGCGGCTGCAGACGGCCGTGCGCTCTGCGT
GAGCTGAGCGTAGACCTGCGGGCCGAGCGCTCGGTGCTCATCCCCGAGAC
ATACCAGGCCAACAACTGCCAGGGGGCCTGCGGCTGGCCTCAGTCGGACC
GCAACCCGCGCTACGGCAACCACGTGGTGCTGCTGCTAAAGATGCAGGCC
CGCGGCGCCACCCTGGCGCGCCCGCCCTGCTGTGTGCCCACAGCCTACAC
CGGCAAGCTCCTCATCAGCCTGTCCGAGGAGCGCATCAGTGCGCACCACG
TCCCAAACATGGTGGCCACCGAATGCGGCTGCCGGTGACCTCGCGCCGTG
CTCCTCGTGCTGCCCCGGCCCGTATTTATTCGGACCCCGTCATTGCCCCA
TTAAACACGGGAAGGC
```
(the sequence of bovine cDNA); and (b) DNA sequences which hybridize to the aforementioned DNA sequences and which code on expression for a human MIS-like polypeptide or a bovine MIS-like polypeptide and preferably have a substantial degree of homology (more preferably, at least about 70% homology and most preferably at least about 80% of homology) to the aforementioned DNA sequences; and (c) DNA sequences which code on expression for a polypeptide coded for on expression by any of the foregoing DNA sequences. Recombinant DNA molecules containing these DNA sequences, hosts transformed with them and MIS-like polypeptides coded for on expression by them are also part of this invention.

The DNA sequences, recombinant DNA molecules, hosts and processes of this invention enable the production of MIS-like polypeptides for use in the treatment of ovarian cancer and other susceptible cancers.

Also within the scope of the present invention are the polypeptides selected from the group consisting of

```
MRDLPLTSLALVLSALGALLGTEALRAEEPAVGTSGLIFREDLDWPPGIP
QEPLCLVALGGDSNGSSSPLRVVGALSAYEQAFLGAVQRARWGPRDLATF
GVCNTGDRQAALPSLRRLGAWLRDPGGQRLVVLHLEEVTWEPTPSLRFQE
PPPGGAGPPELALLVLYPGPGPEVTVTRAGLPGAQSLCPSRDTRYLVLAV
DRPAGAWRGSGLALTLQPRGEDSRLSTARLQALLFGDDHRCFTRMTPALL
LLPRSEPAPLPAHGQLDTVPFPPPRPSAELEESPPSADPFLETLTRLVRA
LRVPPARASAPRLALDPDALAGFPQGLVNLSDPAALERLLDGEEPLLLLL
RPTAATTGDPAPLHDPTSAPWATALARRVAAELQAAAAELRSLPGLPPAT
APLLARLLALCPGGPGGLGDPLRALLLLKALQGLRVEWRGRDPRGPGRAQ
RSAGATAADGPCALRELSVDLRAERSVLIPETYQANNCQGVCGWPQSDRN
PRYGNHVVLLLKMQARGAALARPPCCVPTAYAGKLLISLSEERISAHHVP
NMVATECGCR
```
(the complete amino acid sequence of human MIS protein);

```
RAEEPAVGTSGLIFREDLDWPPGIPQEPLCLVALGGDSNGSSSPLRVVGA
LSAYEQAFLGAVQRARWGPRDLATFGVCNTGDRQAALPSLRRLGAWLRDP
GGQRLVVLHLEEVTWEPTPSLRFQEPPPGGAGPPELALLVLYPGPGPEVT
VTRAGLPGAQSLCPSRDTRYLVLAVDRPAGAWRGSGLALTLQPRGEDSRL
STARLQALLFGDDHRCFTRMTPALLLLPRSEPAPLPAHGQLDTVPFPPPR
PSAELEESPPSADPFLETLTRLVRALRVPPARASAPRLALDPDALAGFPQ
GLVNLSDPAALERLLDGEEPLLLLLRPTAATTGDPAPLHDPTSAPWATAL
ARRVAAELQAAAAELRSLPGLPPATAPLLARLLALCPGGPGGLGDPLRAL
LLLKALQGLRVEWRGRDPRGPGRAQRSAGATAADGPCALRELSVDLRAER
SVLIPETYQANNCQGVCGWPQSDRNPRYGNHVVLLLKMQARGAALARPPC
CVPTAYAGKLLISLSEER!SAHHVPNMVATECGCR
```
(the amino acid sequence of mature human MIS protein);

```
MPGPSLSLALVLSAMGALLRPGTPREEVFSTSALPREQATGSGALIFQQA
WDWPLSSLWLPGSPLDPLCLVTLHGSGNGSRAPLRVVGVLSSYEQAFLEA
VRRTHWGLSDLTTFAVCPAGNGQPVLPHLQRLQAWLGEPGGRWLVVLHLE
EVTWEPTPLLRFQEPPPGGASPPELALLVVYPGPGLEVTVTGAGLPGTQS
LCLTADSDFLALVVDHPEGAWRRPGLALTLRRRGNGALLSTAQLQALLFG
ADSRCFTRKTPALLLLLPARSSAPMPAHGRLDLVPFPQPRASPEPEEAPP
SADPFLETLTRLVRALAGPPARASPPRLALDPGALAGFPQGQVNLSDPAA
LERLLDGEEPLLLLLPPTAATTGVPATPQGPKSPLWAAGLARRVAAELQA
VAAELRALPGLPPAAPPLLARLLALCPGNPDSPGGPLRALLLLKALQGLR
AEWRGRERSGSARAQRSAGAAAADGPCALRELSVDLRAERSVLIPETYQA
NNCQGACGWPQSDRNPRYGNHVVLLLKMQARGATLARPPCCVPTAYTGKL
LISLSEERISAHHVPNMVATECGCR
```
(tne complete amino acid sequence of bovine MIS protein):

```
REEVFSTSALPREQATGSGALIFQQAWDWPLSSLWLPGSPLDPLCLVTLH
GSGNGSRAPLRVVGVLSSYEQAFLEAVRRTHWGLSDLTTFAVCPAGNGQP
VLPHLQRLQAWLGEPGGRWLVVLHLEEVTWEPTPLLRFQEPPPGGASPPE
LALLVVYPGPGLEVTVTGAGLPGTQSLCLTADSDFLALVVDHPEGAWRRP
GLALTLRRRGNGALLSTAQLQALLFGADSRCFTRKTPALLLLLPARSSAP
```

-continued
MPAHGRLDLVPFPQPRASPEPEEAPPSADPFLETLTRLVRALAGPPARAS
PPRLALDPGALAGFPQGQVNLSDPAALERLLDGEEPLLLLLPPTAATTGV
PATPQGPKSPLWAAGLARRVAAELQAVAAELRALPGLPPAAPPLLARLLA
LCPGNPDSPGGPLRALLLLKALQGLRAEWRGRERSGSARAQRSAGAAAAD
GPCALRELSVDLRAERSVLIPETYQANNCQGACGWPQSDRNPRYGNHVVL
LLKMQARGATLARPPCCVPTAYTGKLLISLSEERISAHHVPNMVATECGC
R (the amino acid sequence of mature bovine MIS protein); and MIS-like polypeptides related thereto, an anti-cancer pharmaceutical composition comprising one of the foregoing polypeptides and a pharmaceutically acceptable carrier and methods of using such compositions in treating susceptible cancers, especially cancers of the female genital tract (e.g., ovarian cancer).

BRIEF DESCRIPTION OF THE DRAWINGS

FIG. 1 depicts the amino acid sequences obtained from sequence analysis of tryptic peptides of bovine MIS. Only two of the 23 sequences obtained are shown.

FIG. 2 shows the sixteen pools of chemically synthesized oligonucleotide DNA probes that were used to isolate the bovine cDNA clone.

FIG. 3 (A-H) displays the nucleotide sequence of the bovine gene which includes the full length cDNA sequence and the promoter region.

FIG. 4 depicts the construction of plasmid pBG311.bmis which may be used to express the bovine DNA sequence of the invention.

FIG. 6 (A-K) displays the nucleotide sequence of the human gene in cosmid clone chmis33. The protein sequence is indicated below the DNA sequence. It is interrupted in four places by introns.

FIG. 7 depicts the construction of plasmids pBG311.hmis and pBG312.hmis that may be used to express the human DNA sequence of the invention.

Figure 5:
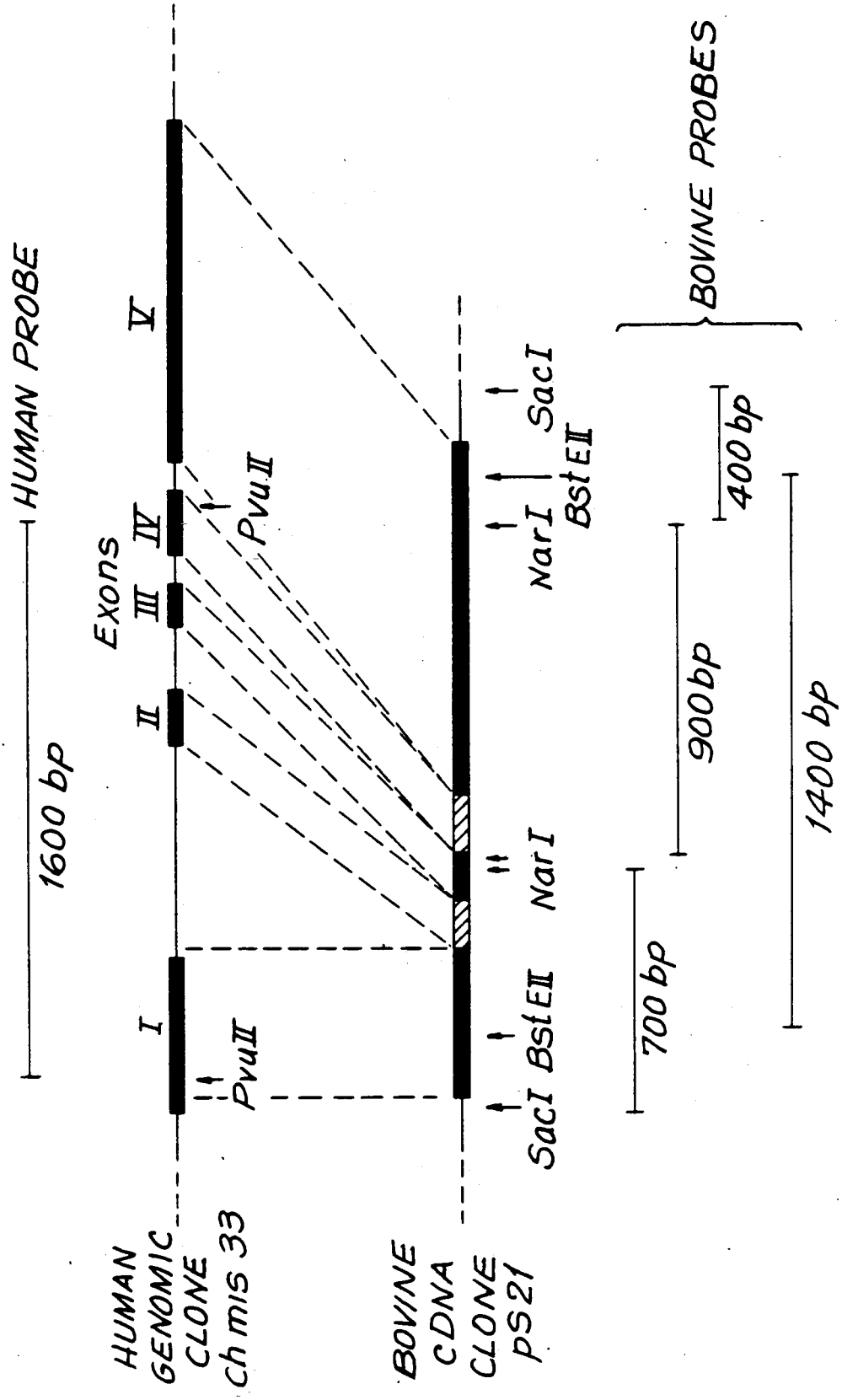
FIG. 5 depicts the human genomic clone chmis33 and compares it with the bovine cDNA clone pS21. The solid blocks are exons which contain the protein coding regions.

In order that the invention herein described may be more fully understood, the following detailed description is set forth.

In the description, the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during the translation of mRNA into amino acid sequences. During translation the proper reading frame must be maintained. For example, the DNA sequence GCTGGTTGTAAG may be expressed in three reading frames or phases, each of which affords a different amino acid sequence:

GCTGGTTGTAAG—Ala-Gly-Cys-Lys
G CTGGTTGTA AG —Leu-Val-Val
GC TGGTTGTAA G--Trp-Leu-(STOP)

Polypeptide—A linear array of amino acids connected one to the other by peptide bonds between the α-amino and carboxy groups of adjacent amino acids.

Genome—The entire DNA of a cell or a virus. It includes, inter alia, the structural gene coding for the polypeptides of the substance, as well as operator, promoter and ribosome binding and interaction sequences, including sequences such as the Shine-Dalgarno sequences.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a gene or DNA sequence to produce a polypeptide. It is a combination of transcription and translation.

cDNA clone—A clone containing a DNA insert that was synthesized from mRNA and does not contain introns. The vector can be a plasmid or a phage.

Genomic clone—A clone containing a DNA insert which is a fragment of a genome (i.e., isolated from total cellular DNA). It can contain introns which interrupt the protein coding region of the gene. The vector can be a plasmid, a phage or a cosmid.

Exon—Portions of the gene which after transcription are maintained in the mRNA following splicing of the precursor RNA.

Intron—Portions of the gene which are spliced out after transcription.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (TET$^R$) transforms a cell previously sensitive to tetracycline into one which is resistant to it. A cell transformed by a plasmid is called a "transformant".

Phage or Bacteriophage—Bacterial virus many of which consist of DNA sequences encapsidated in a protein envelope or coat ("capsid").

Cosmid—A plasmid containing the cohesive end ("cos") site of bacteriophage λ. Cosmids may, because of the presence of the cos site, be packaged into λ coat protein and used to infect an appropriate host. Because of their capacity for large fragments of foreign DNA, cosmids are useful as cloning vehicles.

30 Cloning Vehicle—A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

Expression Control Sequence—A sequence of nucleotides that controls and regulates expression of genes when operatively linked to those genes. They include the lac system, the β-lactamase system, the trp system, the tac and trc systems, the major operator and promoter regions of phage λ, the control region of fd coat protein, the early and late promoters of SV40, promoters derived from polyoma virus and adenovirus, metallothionine promoters, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells and their viruses or combinations thereof. For mammalian cells the gene can be linked to a eukaryotic promoter such as that for the SV40 early region coupled to the gene encoding dihydrofolate reductase and selectively amplified in Chinese hamster ovary cells to produce a cell line containing many copies of actively transcribed eukaryotic genes.

MIS-Like Polypeptide—A polypeptide displaying a biological or immunological activity of an MIS protein. As used herein, the phrase "biological activity of an MIS protein" shall be understood to mean that the MIS-like polypeptide has a cross section of biological activity which is substantially similar to that of a natural MIS protein (e.g., it is able to stimulate regression of the Mullerian ducts or is cytotoxic to one or more types of ovarian tumor cells, for example, the cell line HOC-21, and preferably, it both stimulates regression of the Mullerian ducts and is cytotoxic to one or more types of ovarian tumor cells). As used herein, the phrase "immunological activity of an MIS protein" shall be understood to mean the ability of an MIS-like polypeptide to cross-react with an antibody which is specific for a natural MIS protein. An example of such an antibody is disclosed in U.S. Pat. No. 4,487,833. An MIS-like polypeptide may include amino acids in addition to those of a native MIS protein or it may not include all of the amino acids of native MIS protein. For example, it may include an N-terminal methionine. Also, this polypeptide may be a mature protein or an immature protein or a protein derived from an immature protein (for example, a protein wherein only a portion of the signal sequence has been cleaved). Examples of such polypeptides are derivatives of MIS polypeptides which have been prepared by modification of the MIS amino acid sequence to achieve an improvement in properties, e.g., greater storage stability or increased half-life in vivo. As used herein, the phrase "MIS-like polypeptides derived therefrom" shall be understood to mean not only a claimed MIS-polypeptide (e.g., bovine MIS or human MIS) but also various related polypeptides of the types described in this paragraph.

The present invention relates to DNA sequences and recombinant DNA molecules coding for MIS polypeptides and processes for the production of those polypeptides.

In our isolation and cloning of a DNA sequence of this invention, we adopted a selection strategy based upon bovine MIS protein. Accordingly, we purified a bovine MIS protein from bovine testes and determined the amino acid sequence of various fragments of that protein. Based on those protein sequences, we then synthesized several antisense oligonucleotide DNA probes corresponding to those regions of purified bovine protein which had minimal nucleotide degeneracy. We then used these probes to screen a bovine cDNA library comprising E.coli cells containing bovine testis cDNA sequences inserted into a phage cloning vector.

For screening, we hybridized the oligonucleotide probes to the bovine cDNA library utilizing a plaque hybridization screening assay and we selected clones hybridizing to a number of our probes. After isolating and subcloning the selected bovine cDNA inserts into plasmids, we determined their nucleotide sequences and compared them to our amino acid sequences from peptides of purified bovine MIS protein. As a result of this comparison, we found that the nucleotide sequences of all clones isolated coded for amino acid sequences of bovine MIS protein.

We used the insert of one bovine MIS cDNA clone (pS21) to isolate the human MIS gene from a human cosmid library and a partial cDNA clone from a human cDNA library. We made the human cDNA library from total RNA extracted from newborn human testis.

The cDNA sequences or genomic DNA sequences of this invention can be operatively-linked to expression control sequences and used in various mammalian or other eukaryotic or prokaryotic host cells to produce the MIS-like polypeptides coded for by them. In addition, the cDNA sequences or genomic DNA sequences of the invention are useful as probes to screen human cDNA libraries for other sequences coding for MIS-like polypeptides.

The human genomic DNA sequence, described above, has several introns. DNA sequences and recombinant DNA molecules wherein one or more or all of these introns are deleted are also considered to be within the scope of the present invention.

The bovine and human MIS-like polypeptides (and preferably the human MIS-like polypeptides) of this invention are useful as anti-cancer drugs. For example, such compositions may comprise an anti-cancer effective amount of MIS-like polypeptide of this invention and a pharmaceutically acceptable carrier. Such therapies generally comprise a method of treating patients in a pharmaceutically acceptable manner with those compositions.

Generally, the pharmaceutical compositions of the present invention may be formulated and administered using methods similar to those used for other pharmaceutically important polypeptides (e.g., alpha-interferon). Thus, the polypeptides may be stored in lyophilized form, reconstituted with sterile water just prior to administration, and administered intravenously. Preferably, the pharmaceutical formulations of the present invention will be administered in dosages and modes of administration similar to those that have been used for MIS protein as disclosed in U.S. Pat. No. 4,510,131, the disclosure of which is hereby incorporated herein by reference.

A wide variety of host/cloning vehicle combinations may be employed in cloning or expressing the MIS-like polypeptide DNA sequences prepared in accordance with this invention. For example, useful cloning or expression vehicles may consist of segments of chromosomal, non-chromosomal and synthetic DNA sequences, such as various known derivatives of SV40 and known bacterial plasmids, e.g., plasmids from *E.coli* including col El, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and filamentous single-stranded DNA phages and vectors derived from combinations of plasmids and phage DNAs such as plasmids which have been modified to employ phage DNA or other expression control sequences or yeast plasmids such as the 2μ plasmid or derivatives thereof. For cDNA cloning, the preferred expression vector is λgt10 and the preferred host is *E.coli* BNN102. For animal cell expression, the preferred expression vectors are pBG311 and pBG312 in Chinese hamster ovary (CHO) cells.

Within each specific cloning or expression vehicle, various sites may be selected for insertion of the MIS-like polypeptide DNA sequences of this invention. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

Various expression control sequences may also be chosen to effect the expression of the DNA sequences of this invention. These expression control sequences include, for example, the lac system, the β-lactamase system, the trp system, the tac system, the trc system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, promoters for mammalian cells such as the SV40 early promoter, adenovirus late promoter and metallothionine promoter, and other sequences known to control the expression of genes of prokaryotic or eukaryotic cells or their viruses and various combinations thereof. In mammalian cells, it is additionally possible to amplify the expression units by linking the gene to that for dihydrofolate reductase and applying a selection to host Chinese hamster ovary cells.

For expression of the DNA sequences of this invention, these DNA sequences are operatively-linked to one or more of the above-described expression control sequences in the expression vector. Such operative linking, which may be effected before or after the chosen MIS-like polypeptide DNA sequence is inserted into a cloning vehicle, enables the expression control sequences to control and promote the expression of the DNA sequence.

The vector or expression vehicle, and in particular the sites chosen therein for insertion of the selected DNA fragment and the expression control sequence employed in this invention, is determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site for a particular MIS-like polypeptide sequence is determined by a balance of these factors, not all selections being equally effective for a given case.

It should also be understood that the DNA sequences coding for the MIS-like polypeptides of this invention that are inserted at the selected site of a cloning or expression vehicle may include nucleotides which are not part of the actual gene coding for the MIS-like polypeptide or may include only a fragment of the entire gene for that polypeptide. It is only required that whatever DNA sequence is employed, a transformed host will produce a MIS-like polypeptide. For example, the MIS-like polypeptide-related DNA sequences of this invention may be fused in the same reading frame in an expression vector of this invention to at least a portion of a DNA sequence coding for at least one eukaryotic or prokaryotic carrier protein or a DNA sequence coding for at least one eukaryotic or prokaryotic signal sequence, or combinations thereof. Such constructions may aid in expression of the desired MIS-like polypeptide-related DNA sequence, improve purification or permit secretion, and preferably maturation, of the MIS-like polypeptide from the host cell. The MIS-like polypeptide-related DNA sequence may alternatively include an ATG start codon, alone or together with other codons, fused directly to the sequence encoding the first amino acid of a mature native MIS-like polypeptide. Such constructions enable the production of, for example, a methionyl or other peptidyl-MIS like polypeptide, that is part of this invention. This N-terminal methionine or peptide may either then be cleaved intra- or extra-cellularly by a variety of known processes or the MIS-like polypeptide with the methionine or peptide attached may be used, uncleaved, in the pharmaceutical compositions and methods of this invention.

The cloning vehicle or expression vector containing the MIS-like polypeptide coding sequences of this invention is employed in accordance with this invention to transform an appropriate host so as to permit that host to express the MIS-like polypeptides for which the DNA sequence codes.

Useful cloning or expression hosts may include strains of *E.coli*, such as *E.coli* C600, *E.coli* ED8767, *E.coli* DH1, *E.coli* LE392, *E.coli* HB 101, *E.coli* X1776, *E.coli* X2282, *E.coli* MRCI, *E.coli* BNN102, *E.coli* JM83, *E.coli* JA221, and strains of Pseudomonas, Bacillus, and Streptomyces, yeasts and other fungi, animal hosts, such as CHO cells, COS cells or mouse cells, other animal (including human) hosts, plant cells in culture or other hosts.

The selection of an appropriate host is also controlled by a number of factors recognized by the art. These include, for example, compatibility with the chosen vector, toxicity of proteins encoded by the hybrid plasmid, susceptibility of the desired protein to proteolytic degradation by host cell enzymes, contamination or binding of the protein to be expressed by host cell proteins difficult to remove during purification, ease of recovery of the desired protein, expression characteristics, bio-safety and cost. A balance of these factors must be struck with the understanding that not all host vector combinations may be equally effective for either the cloning or expression of a particular recombinant DNA molecule.

It should be understood that the MIS-like polypeptides (prepared in accordance with this invention in those hosts) may include polypeptides in the form of fused proteins (e.g., linked to a prokaryotic, eukaryotic or combination N-terminal segment to direct excretion, improve stability, improve purification or improve possible cleavage of the N-terminal segment), in the form of a precursor of MIS-like polypeptides (e.g., starting with all or parts of a MIS-like polypeptide signal sequence or other eukaryotic or prokaryotic signal sequences), in the form of a mature MIS-like polypeptide, or in the form of an fmet-MIS-like polypeptide. As pointed out above, the phrase "MIS-like polypeptides derived therefrom", as used herein, shall be understood to include such MIS-like polypeptides.

One particularly useful form of a polypeptide in accordance with this invention, or at least a precursor thereof, is a mature MIS-like polypeptide with an easily cleaved amino acid or series of amino acids attached to the amino terminus. Such construction allows synthesis of the polypeptide in an appropriate host, where a start signal that may not be present in the mature polypeptide is needed, and then cleavage in vivo or in vitro of the extra amino acids to produce mature MIS-like polypeptides. Such methods exist in the art. See, e.g., U.S. Pat. Nos. 4,332,892, 4,338,397, and 4,425,437. The polypeptides may also be glycosylated, like native MIS protein, unglycosylated, or have a glycosylation pattern different than that of native MIS protein. Such glycosylation will result from the choice of host cell or post-expression treatment chosen for the particular inhibitor.

The polypeptides of the invention also include MIS-like polypeptides that are coded for on expression by DNA sequences characterized by different codons for some or all of the codons of the present DNA sequences. These substituted codons may code for amino acids identical to those coded for by the codons replaced but result in higher yield of the polypeptide. Alternatively, the replacement of one or a combination of codons leading to amino acid replacement or to a longer or shorter MIS-like polypeptide may alter its properties in a useful way (e.g., increase the stability, increase the solubility or increase the therapeutic activity).

In order that this invention may be better understood, the following examples are set forth. These examples are for purposes of illustration only and are not to be construed as limiting the scope of the invention in any manner.

EXAMPLES

EXAMPLE 1

SEQUENCING OF BOVINE MIS PROTEIN

We isolated bovine MIS protein from newborn bovine testis by the procedure of Budzik et al. (*Cell*, 34, 307–314 (1983)). After eluting it from the Matrix Gel Green A column with 0.5M NaCl, we concentrated the bovine MIS fraction (Green-3) and dialyzed against PBS and 0.01% Nonidet-P40 and stored at −70°.

Analytical reducing SDS-PAGE indicated that MIS (Green-3 fraction) contained two predominant polypeptides of 74 Kd and 70 Kd, and several minor components including species near 140 and 95 Kd. We obtained highly purified samples of the 74 and 70 Kd species by combination of semi-prep SDS-PAGE followed by electroelution. Each of these was subjected to N-terminal analysis. Both the 70 Kd and the 74 Kd polypeptides had the same N-terminus (ArgGluGluVal-PheSer).

We separately digested approximately 1 nanomole each of the reduced and carboxymethylated 74 Kd and 70 Kd MIS polypeptides with TPCK-trypsin. After carboxymethylation, we resuspended purified polypeptides in 0.1M $NH_4HCO_3$ plus 0.1 mM $CaCl_2$, and then incubated with TPCK trypsin for 16 h at 37° C. During this incubation, we added trypsin three times to a final concentration of 2.0% of total protein at time zero, 4.0% after 4 h and 6.0% after 12 h.

We resolved the cleavage fragments from these digestions by high pressure liquid chromatography utilizing a gradient of acetonitrile from 0–75% in 0.1% trifluoroacetic acid to elute peptides bound to a C18 column. The two tryptic maps were very similar, indicative of the same primary structure and suggesting that the 70 Kd polypeptide derives from the 74 Kd polypeptide. Therefore, we combined selected conserved peaks from each digest and subjected them to sequence analysis using a gas phase sequencer (Applied Biosystems 470A). We analyzed PTH-amino acids by high pressure liquid chromatography on a 5 μm cyano column (Hypersil), using a gradient of acetonitrile:methanol (4:1) from 15–55% in 0.02M sodium acetate (pH 5.7).

Tryptic digestion produced over 20 peaks. Six of these yielded protein sequence. The sequence of one tryptic peptide, #T105-106, is shown in FIG. 1.

Analytical digests of $^{125}$I-labelled 74 Kd and 70 Kd MIS by trypsin or *S. aureus* V8 protease showed that most of the peptides generated were larger than 10 Kd and were recovered in low yield by HPLC on a C18 column. Using both SDS-urea PAGE and HPLC analysis, we again observed that conserved cleavage products occurred between 70 Kd and 74 Kd MIS, confirming that the two polypeptides are related.

In order to increase the extent of digestion by TPCK-trypsin at basic pH, we succinylated 1 nmole of MIS prior to digestion, and separated the resultant peptides on a C8 column (90% yield). We obtained six more peptide sequences, ranging from 5 to 16 residues; two of these confirmed previously obtained sequences. The sequence of tryptic peptide #T81 is shown in FIG. 1.

We further improved the efficiency of digestion of MIS by TPCK-trypsin by including 2M urea in the digestion. Using peptides produced in this manner, we obtained eleven additional peptide sequences. In total, we obtained 23 peptide sequences, two of which are shown in FIG. 1.

EXAMPLE 2

SYNTHESIS OF OLIGONUCLEOTIDE DNA PROBES

After the amino acid sequences of various regions of the bovine MIS protein were determined (see FIG. 1), we chemically synthesized two pools of antisense oligonucleotide DNA probes that coded for some of those protein sequences (see FIG. 2). We synthesized the two pools (1-4 and 9-12) shown in FIG. 2 because they corresponded to regions of the MIS protein that have minimal nucleic acid degeneracy. For each amino acid sequence, we synthesized mixtures of probes complementary to all possible codons. The probes were complementary to the DNA sequences which code for the amino acid sequence, i.e., the probes were antisense, to enable the probes to recognize the corresponding sequences in mRNA as well as in DNA. The amino acid sequences of the two selected regions of the MIS protein and all the possible nucleotide codon combinations that encode them are shown in FIG. 2. Coding degeneracies are indicated as follows: N =C, T, A, or G; R =A or G; Y =C or T; and H =A, C, or T.

The two pools of the probes, derived from sequences in the tryptic fragments T105-106 and T81 of FIG. 1, were 17-mers with 256 fold degeneracy or 20-mers with 512 fold degeneracy respectively. We synthesized each pool in groups of four, by splitting at a degenerate codon in the middle of the probe. Thus, we prepared the 256 fold degenerate 17-mer of T105-106 in four subpools [1-4] of 64 and the 512 fold degenerate 20-mer of T81 in four pools [9-12] of 128. This allowed us to reduce the degeneracy by using them individually on Northern blots in order to distinguish the subpool that contained the correct sequence (see below). We synthesized probes on an Applied Biosystems 380A DNA synthesizer and purified them by gel electrophoresis. We labelled the probes by using [δ-32P]-ATP and polynucleotide kinase (Maxam and Gilbert, *Proc. Natl. Acad. Sci.*, 74, 560 (1977)).

We used Northern analysis to reduce the degeneracy of the two probe regions 1-4 and 9-12. We hybridized the probes individually to Northern blots with RNA from two-week old and three-month old bovine testis, and adult bovine kidney. Since only two-week old bovine testis contains biologically active MIS, we expected that the Northern analysis would distinguish which probe within a group contained the correct MIS sequence. The less degenerate probe would then be used to screen the cDNA library. Northern blots with MIS probes 1-4 suggested that probe 2 contained the correct oligomer sequence, while Northern blots with MIS probes 9-12 indicated that probe 12 contained the correct oligomer sequence. In both cases, a 2000 nucleotide transcript was observed in the RNA from two week old bovine testis, and not in the other RNAs. We broke subpool 2 into four subpools (13-16) of 16-fold degeneracy, while probe 12 was broken into four subpools (17-20) of 32-fold degeneracy. Northern analysis with these probes confirmed that the correct choices were made, since one subpool from probe region 1-4 (16) and one subpool from probe region 9-12 (18) both hybridized to a 2000 nucleotide transcript in the two-week old bovine testis RNA. The transcript was not present in three month old bovine testis or kidney.

EXAMPLE 3

CONSTRUCTION AND SCREENING OF A BOVINE TESTIS cDNA LIBRARY

We constructed a bovine cDNA library from poly A+ mRNA isolated from bovine testis. We inserted the cDNA sequences into λgt10 and amplified the sequences in *E.coli* BNN 102 cells.

A. Extraction of RNA from Bovine Testis

We obtained testis from two week old calves immediately after slaughter. We removed the semi-niferous tubules from the tunica albuginea and quickly froze them in liquid nitrogen. We pulverized about 10 g of the frozen tissue and homogenized the resulting material in 100 ml of extraction buffer (4M guanidine thiocyanate, 0.5% SDS, 25mM sodium citrate, 0.1% Sigma antifoam) using a polytron for 2 min at high speed. We centrifuged the homogenate for 20 min at 8,000 rpm in a Sorvall RC2B centrifuge at 4° C. We recovered 75 ml of the supernatant and layered it on 30 ml (3 tubes containing 10 ml each) of a CsCl cushion (5.7M CsCl, 25mM NaOAc pH 5.0, 1 mM EDTA) and then centrifuged it in a SW28 rotor at 22,000 rpm for 16 hrs. We resuspended the pellets in 10 ml of 10 mM Tris-HCl (pH 7.4), 1 mM EDTA, and 0.1% SDS. We then ethanol-precipitated the nucleic acids in 0.3M sodium acetate at −20° C. overnight and pelleted them at 14K rpm in a Sorvall RC2B centrifuge (SS34 rotor) at 4° C for 20 min. We resuspended the pellets in 5 ml 0.3M sodium acetate, and again ethanol-precipitated the nucleic acids as described above. We resuspended the final pellet in 300 µl H₂O and stored it at −20° C. We enriched this RNA preparation for poly(A)+ RNA by passage over an oligo(dT)-cellulose column (PL Biochem).

B. Construction Of A cDNA Library From Two Week Old Bovine Testis Poly A+ mRNA In λGT10

1. cDNA Synthesis

We synthesized cDNA from 25 µg poly A+ mRNA isolated from two week old bovine testis as described above. We diluted the mRNA to 500 µg/ml in H₂O and denatured by treatment with methyl-mercury hydroxide (CH₃HgOH). We then added 1M CH₃HgOH (Alfa Venetron) to 50mM. 5 µl of 50mM CH₃HgOH was added to 25 µg of mRNA in 50 µl H₂O and incubated for 10 min. at room temperature. We terminated the reaction by adding 10 µl of 1.4M β-mercaptoethanol.

We then added the denatured mRNA mixture to a reaction mixture consisting of 0.1M Tris-HCl (pH 8.3) at 42° C., 0.01M MgCl₂, 0.01M DTT, 1 mM dATP, 0.5 mM dCTP and 50 µCi³H-dCTP (25.7 Ci/mmol, New England Nuclear), 1 mM dGTP, 1 mM dTTP, 2.5 mM Vanadyl Ribonucleoside complex (Bethesda Research Labs), 20 µg oligo dT 12-18 (PL Biochem), and 196 U AMV Reverse Transcriptase (Seikagaku America). The final volume of the reaction mixture was 200 µl. We incubated the mixture for 3 minutes at room temperature and 3 hours at 44° C. and then terminated the reaction by adding 1/20 vol. 0.5M Na₂EDTA (pH 8.0).

We then extracted the reaction mixture with a mixture of TE saturated phenol and chloroform (50:50). (TE buffer is 10 mM Tris-HCl, pH 7.0, 1 mM Na₂-EDTA.) We then re-extracted the organic phase with TE buffer and we chromatographed the combined aqueous phases through a 5 ml sterile pipet containing a 7×29 cm bed of Sephadex G150 in 0.01M Tris-HCl (pH 7.4), 0.1M NaCl, 0.01M Na2EDTA, 0.05% SDS. We counted an aliquot of each fraction in an LKB liquid scintillation counter. We pooled the front peak minus tail and we precipitated the cDNA with 2.5 vol. 95% ethanol at −20° C. The yield of cDNA was 8.1 µg obtained as a cDNA-mRNA hybrid.

2. Double Strand Synthesis 1 We resuspended the cDNA in H$_2$O and we set up duplicate second strand reactions each containing 4 μg cDNA. Each 400 μl reaction contained 0.02M Tris-HCl pH 7.5, 0.1M KCl, 0.005M MgCl$_2$, 0.5mM dATP+100 μCi α-dATP$^{32}$ (3000 Ci/mmol, New England Nuclear), 1 mM dCTP, 1 mM dGTP, 1 mM dTTP, 100 u DNA Pol 1 Klenow Fraction (Boehringer Mannheim), and 4 U RNase H (P. L. Biochem). We incubated the reactions for 1 hour at 12° C., 1.5 hour at room temperature and then terminated the reactions by addition of 1/20 vol. 0.5M Na$_2$EDTA pH 8.0. We then extracted the reaction mixtures with phenol:chloroform as in the cDNA synthesis step described in the preceding paragraph and precipitated the extracted material by addition of 0.2 vol. 10M ammonium acetate and 2.5 vol. 95% ethanol at −70° C. for 20 min. We warmed the resulting mixtures to room temperature, and then spun for 15 min. in an Eppendorf centrifuge to pellet the double stranded cDNA. We resuspended the pellets in TE Buffer and repeated the precipitation with ammonium acetate (2M final concentration) and ethanol two times.

We dried the pellets in a speed vac and then resuspended them in 100 μl TE buffer. We then added 25 μg boiled RNase A (Sigma), incubated the mixture at 37° C. for 30 min., extracted with phenol:chloroform and chromatographed through Sephadex G150 as described above for the cDNA synthesis step.

To assure blunt ends, we resuspended the double stranded cDNA in H$_2$O and added it to a reaction mixture containing 0.033M Tris acetate pH 7.8, 0.066M potassium acetate, 0.01M Mg acetate, 0.17 mM DTT, 88 μg BSA, 0.25mM dATP, dCTP, dGTP, dTTP, and 18 U T$_4$ DNA polymerase (New England Biolabs). The final volume of the reaction was 300 μl We incubated the reaction for 1 hour at 37° C, and then extracted and precipitated with 2M ammonium acetate and 2.5 vol. 95% ethanol two times as described above for the second strand synthesis step.

We then ligated 2 μg of the blunt ended cDNA to a unique oligomer linker, formed by annealing linker 27, a 22-mer with the sequence 5' AATTGAGCT CGA GCG CGG CCG C to 5' phosphorylated linker 28, an 8-mer with the sequence 5' GCG GCC GCG CTC GAG CTC 3'. The annealed linker contained a phosphorylated blunt end for ligation to blunt end cDNA and a nonphosphorylated 5' protruding sequence (AATT) for ligation to EcoRl digested λgt10. The linker contained recognition sequences for the following restriction enzymes: AluI, AvaI, Ban2, Bsp12, Fnu4H, FnuD2, Ha13, Hgi A1, HhaI, HinPl, NotI, SstI, XhoI, Xma3.

We ligated 2 μg of linker 27-28 to 2 μg cDNA in 0.05M Tris-HCl pH 7.8, 0.01M MgCl$_2$, 0.03M NaCl, 1 mM Spermidine, 0.2mM Na$_2$EDTA, 2mM DTT, 100 μg/ml BSA, 0.4mM ATP, and 1000 U T$_4$ DNA ligase (New England Biolabs) in 26 μl final vol. at 4° C. for 24 hours. In order to remove excess linker and to size fractionate the cDNA, we extracted the ligation reaction with a mixture of TE saturated phenol and chloroform. We re-extracted the organic layer with TEN Buffer (0.01M Tris-HCl pH 7.5, 0.1M NaCl, and 1 mM Na$_2$EDTA) and the combined aqueous layers were chromatographed on a 1×30 cm Biogel A50 (BioRad) column which had been previously equilibrated in TEN buffer. We ran aliquots of the column fractions on a 1% agarose gel in TBE buffer (0.089M Tris-HCl, 0.089M boric acid and 2.5mM Na$_2$EDTA) and we dried the gel and exposed it to Kodak XAR-5 film at −70° C. We pooled fractions containing cDNA larger than 500 bp and ethanol precipitated them. The yield of size fractionated double stranded cDNA was 900 ng.

3. Library Construction

We mixed 6 μg of EcoRl cut λgt10 with 250 ng cDNA in 0.05M Tris-HCl pH 7.8, 0.01M MgCl$_2$, 0.03M NaCl, 1 mM Spermidine, 0.2mM Na$_2$EDTA, 2mM DTT, and 100 μg/ml BSA in 31.2 μl. We heated these components to 70° C. for 3 min., 45° C. for 15 min., cooled on ice, and then spun them for 5 sec in an Eppendorf centrifuge. We adjusted the reaction mixture to 0.25 mM ATP and 2000 U T$_4$ DNA ligase (NEB) and then incubated for 16 hours at 15° C. We packaged 3.4 μl aliquots of the ligation into phage particles using Amersham packaging mix, according to the protocol supplied by Amersham, and used the packaged DNA to infect E.coli BNN102 cells. Plating of the library yielded 5.4×10$^6$ independent plaques which we amplified and CsCl banded. 41% of the plaques had inserts which indicated a library complexity of 2.2×10$^6$ recombinants. The titer of the CsCl banded phage was 1.6×10$^{13}$ PFU/ml.

C. Screening Of The Library

We screened the library with the labeled oligonucleotide probe 16 for nucleotide sequences that encoded MIS protein sequences using the plaque hybridization screening technique of Benton and Davis (*Science*, 196, 180 (1977)).

We pelleted an overnight culture of BNN102 cells in L broth and 0.2% maltose and resuspended it in an equal volume of SM buffer (50mM Tris-HCl, pH 7.5, 100 mM NaCl, 10 mM MgSO$_4$, and 0.01% gelatin). Thereafter, we pre-adsorbed 0.3 ml of cells with 5×10$^4$ phage particles at room temperature for 15 min. We then diluted the suspension to 8 ml in LB plus 10 mM MgSO$_4$ and 0.7% agarose at 55° C. and plated it on LB Mg plates. We made thirty such plates and then incubated the plates at 37° C for approximately 8 hours until plaques were nearly touching. We then chilled the plates at 4° C for 1 hour to allow the agarose to harden.

We then placed nitrocellulose filters onto the plates containing the recombinant plaques for 5 . min.; and then lifted and lysed the filters by placing them onto a pool of 0.5N NaOH/1.5M NaCl for 5 min, and then submerged them for 5 min. in the same buffer. We then neutralized the filters by submerging in 0.5M Tris-HCl (pH 7.4), 1.5M NaCl, two times for 5 min each. We rinsed them for 2 min. in 1M NH$_4$OAc, air dried them, and baked them for 2 hours at 80° C.

We prehybridized and hybridized the filters to oligonucleotide probe 16 in 0.2% polyvinyl-pyrrolidone, 0.2% ficoll (MW 400,000), 0.2% bovine serum albumin, 0.05M Tris-HCl (pH 7.5), 1M sodium chloride, 0.1% sodium pyrophosphate, 1% SDS, 10% dextran sulfate (MW 500,000) and 100 μg/ml tRNA. We detected hybridizing λ-cDNA sequences by autoradiography.

By means of this technique, we picked and rescreened 19 positive plaques at lower density using the same probe.

We isolated the DNA of these clones, digested it with XhoI, and hybridized it with oligomer probes 16 and 18 using the Southern blot technique (E. M. Southern, *J. Mol. Biol.*, 98, pp. 503-18 (1975)). Nine of the clones contained inserted cDNA which hybridized not only to probe 16 that encodes tryptic peptide T105-106, but also to probe 18 that encodes tryptic peptide T81.

We digested the DNA of clone λ8.21 with Sacl, isolated the 2000 bp insert, and subcloned the fragment into pUC18 to produce recombinant plasmid pS21. We also removed the insert of clone λ8.21, using XhoI, and subcloned it unto pUC18 to produce recombinant plasmid pX21. We then sequenced this plasmid by the method of Maxam and Gilbert (*Proc. Natl. Acad. Sci.*, 74, 560 (1977)). This analysis demonstrated that the clone pS21 contained nucleotide sequences which corresponded to the amino acid sequences of the bovine MIS protein. Within the 2000 bp of this insert, were DNA sequences that encoded all 23 peptides that had been sequenced including the mature N-terminus (i.e., Arg Glu Glu Val Phe Ser). The clone contained 30 bp of sequence upstream encoding 10 amino acids of what was presumably a leader sequence.

In order to confirm that the DNA sequence for the entire mature protein had been obtained, we isolated the genomic clone for bovine MIS (cbmis15) from a cosmid library and sequenced the 5' end by the method of Church and Gilbert (*Proc. Natl. Acad. Sci.*, 81, 1991-95 (1984)). This provided sequence upstream from the 5' end of the insert in clone pS21. An ATG was located in the same reading frame as the mature protein sequence, 72 bp upstream of the Arg residue at the mature N-terminus. This 72 bp encodes a 24 amino acid leader. The first 16 or 17 amino acids of this leader appear to constitute a signal sequence, which enables the protein to be secreted (deduced from Von Heijne analysis, *Eur. J. Biochem.*, 133, 17-21 (1983)). The remaining 7 or 8 amino acids are subsequently cleaved off to generate the mature protein. (It is not clear whether this cleavage is necessary to activate the protein.) A promoter sequence TATA is located upstream from the initiating methionine (34 bp) suggesting that the 5' untranslated region is very short. We confirmed this by the following primer extension experiment which showed that RNA initiation occurs about 10 nucleotides upstream of the initiating ATG. An anti-sense kinased oligomer (5'-A*GTCCCAGGCTTGCTGAAAGAT-GAGTGCCC 3') was hybridized to poly A+ RNA from bovine testes and extended with reverse transcriptase. The primer extension product was sized on a sequencing gel at 166-167 nucleotides. This placed the 5' end of the mRNA 10 or 11 nucleotides upstream from the initiating ATG. This analysis proved that we had isolated the entire gene for bovine MIS which encodes for a 58 Kd protein. The DNA sequence is shown in FIG. 3a. The first 100 bp contain the promoter and 5' untranslated region. This is followed by 1875 bp that encode the bovine MIS protein and 81 bp of 3' untranslated sequence.

EXAMPLE 4

ISOLATION OF THE HUMAN GENOMIC CLONE

Using the bovine cDNA clone pS21, we isolated the human clone (chmis33) from a human cosmid library. We sequenced the entire gene, which is contained in five exons that span a distance of 2.8 kb. FIG. 5 shows the general structure of the human gene, while FIG. 6a-k shows the nucleotide sequence. In FIG. 6a, the first 100 bp contain the human promoter and the 5' untranslated region. This is followed by 2622 bp that contain the five protein coding regions, which are indicated below the DNA sequence. The last 112 bp are the 3' untranslated region.

EXAMPLE 5

ISOLATION OF A PARTIAL HUMAN cDNA CLONE

We constructed a cDNA library in λgt10 from 25 μg of total human testis RNA using the procedures described in Example 3. From this library, we isolated a partial clone (λHT4) which contains about 60% of the gene (i.e., from the middle of the fourth exon to the poly A+ site).

Sequence analysis of the clone provided the DNA sequence at the junction of exons IV and V. By comparing the nucleotide sequence of the human genomic clone with the bovine cDNA clone pS21 and using the Chambon "rules" for splicing that have been elucidated, we have generated a proposed sequence for the human cDNA in which all introns have been deleted.

EXAMPLE 6

EXPRESSION OF THE BOVINE GENE

We combined sequences from the bovine cDNA clone (pX21) with sequences from the bovine genomic cosmid clone (cbmis.15) in the animal cell expression vector pBG311 in order to express the entire bovine protein in COS cells and CHO cells (FIG. 4). Expression may be detected by analyzing RNA by Northern and S1 analysis. Also, recombinant bovine MIS may be detected by a RIA and by the organ culture assay. *E.coli* strain JM83 harboring plasmid pBG311.bmis has been deposited with the In Vitro International Inc. depository as Deposit No. IVI 10090.

EXAMPLE 7

EXPRESSION OF THE HUMAN GENE

We isolated the 4.5 kb AflII fragment from the human genomic cosmid clone chmis33 and inserted it in the correct orientation in the animal cell expression vectors pBG311 and pBG312 (FIG. 7). The human gene in these vectors may be expressed in COS cells and CHO cells. The pBG311 vector uses the SV40 early promoter to drive expression, while the pBG312 vector uses the major late adenovirus-2 promoter.

We have detected expression of the human gene in pBG312.hmis in COS cells. We analyzed RNA isolated from COS cells 48 hrs after transfection with pBG312.hmis by Northern and S1 analysis. The S1 analysis clearly demonstrated that the human MIS gene was being transcribed and that the RNA was being spliced. We analyzed the medium for active MIS in the organ culture assay and obtained a 3-grade positive regression of the rat Mullerian duct. We have also stably transformed CHO cells with pBG312.hmis and pBG311.hmis.

*E.coli* strain JA221 harboring plasmid pBG312.hmis has been deposited with In Vitro International Inc. depository as Deposit No. IVI 10089.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodi-

We claim:

1. A DNA sequence selected from the group consisting of the DNA sequences

```
AAGGTCGCGGCAGAGGAGATAGGGGTCTGTCCTGCACAAACACCCCACCT
TCCACTCGGCTCACTTAAGGCAGGCAGCCCAGCCCCTGGCAGCACCCACG
ATGCGGGACCTGCCTCTCACCAGCCTGGCCCTAGTGCTGTCTGCCCTGGG
GGCTCTGCTGGGGACTGAGGCCCTCAGAGCAGAGGAGCCAGCTGTGGGCA
CCAGTGGCCTCATCTTCCGAGAAGACTTGGACTGGCCTCCAGGCATCCCA
CAAGAGCCTCTGTGCCTGGTGGCACTGGGCGGGGACAGCAATGGCAGCAG
CTCCCCCCTGCGGGTGGTGGGGGCTCTAAGCGCCTATGAGCAGGCCTTCC
TGGGGGCCGTGCAGAGGGCCCGCTGGGGCCCCCGAGACCTGGCCACCTTC
GGGGTCTGCAACACCGGTGACAGGCAGGCTGCCTTGCCCTCTCTACGGCG
GCTGGGGGCCTGGCTGCGGGACCCTGGGGGGCAGCGCCTGGTGGTCCTAC
ACCTGGAGGAAGGTATGTGGGGCCCAGCCCCAAGCTTGGCACCGCCGTCT
TCCTTCAGGTGGGCCGGGTCCTCCTAGGGAAGATCAGGGGCTGGCAGAGC
CCCCACCCTGGGCAGGGAGGCTGTGGTCTTGTTCCTAGGACTGGGTTGCG
GGTCCGTGGCCTGGAAGGTGGGCACCACACTCTGTCCTGTCCCCGAAGCC
CAGCTCTTAGACTTGCCCCTGCCTCGGTGCCAGGGAGAGAGCTGCTGCCT
TCTCCCCACCCCTGAAGACGACGCAGGGCTCGGGGCCAGTGGAACCCTTC
TTCCCACAGCCCCAGCCTGTTCTCAGGGCCGCTGGCCTAAGATACTCCCT
GCGGGGAAGGGGCTTCATCGGGCACCCCAACCCAGAGACCCCAGGGCGGC
AGCCCCACCCACAGCCTCAGACGCAGCCCCTGCCTGCCCCTGCCGTCACC
GCTCCCTGGCTGCAGGAAGGCAGCTAAGAGGGGCACCCTTGTCCCCCGCT
TGAGGTCCCCTGCACAGTGGCCAGAGCGGCAGGGACAGATCCCAAAGATT
CCCGGGGGGTGTGGCCTTCAATGGCTCAGGCGTCCCCTGCTGTCCCGGCT
GCAGTGACCTGGGAGCCAACACCCTCGCTGAGGTTCCAGGAGCCCCCGCC
TGGAGGAGCTGGCCCCCAGAGCTGGCGCTGCTGGTGCTGTACCCTGGGC
CTGGCCCTGAGGTCACTGTGACGAGGGCTGGGCTGCCGGGTGCCCAGGTA
CCAGGGAGTTGCATGGGGCAGTGCCCGGGCCGTGGCGGGGGGCATGAATT
TGTTGCAGGGTCTGCAGTACTGAGAACAGCGTAGAACCAGTGGCGATGGG
AGGAAGGGGACCGGTAGAGCGGGGCTGGGTAAGCCTCCATCCAGCCGGGC
TGAGCCCTGGTCTCCGCAGAGCCTCTGCCCCTCCCGAGACACCCGCTACC
TGGTGTTAGCGGTGGACCGCCCTGCGGGGGCCTGGCGGGCTCCGGGCTG
GCCTTGACCCTGCAGCCCCGCGGAGAGGGTAGGTCCGCGTGGAGAGGGAC
GGGGAGCCGGGTCGACTGCCCCCGGGCCCCCAGCCCCTGAGCCAGCCGCG
TGCCCACCCACCGCAGACTCCCGGCTGAGTACCGCCCGGCTGCAGGCACT
GCTGTTCGGCGACGACCACCGCTGCTTCACACGGATGACCCCGGCCCTGC
TCCTGCTGCCGCGGTCCGAGCCCGCGCCGCTGCCTGCGCACGGCCAGCTG
GACACCGTGCCCTTCCCGCCGCCCAGGTGCGCGCAGGCACCGGGACACGG
GGCAGGAGCGGGCGGGGCGGCGTGGCCTCGTGGCCGCTCTCAACTCCTC
CAATTGCGGGTTCCAGGCCATCCGCGGAACTCGAGGAGTCGCCACCCAGC
GCAGACCCCTTCCTGGAGACGCTCACGCGCCTGGTGCGGGCGCTGCGGGT
CCCCCCGGCCCGGGCCTCCGCGCCGGCCGCCTGGCCCTGGATCCGGACGCGC
TGGCCGGCTTCCCGCAGGGCCTAGTCAACCTGTCGGACCCCGCGGCGCTG
GAGCGCCTACTCGACGGCGAGGAGCCGCTGCTGCTGCTGCTGAGGCCCAC
TGCGGCCACCACCGGGGATCCTGCGCCCCTGCACGACCCCACGTCGGCGC
CGTGGGCCACGGCCCTGGCGCGCCGCGTGGCTGCTGAACTGCAAGCGGCG
GCTGCCGAGCTGCGAAGCCTCCCGGGTCTGCCTCCGGCCACAGCCCCGCT
GCTGGCGCGCCTGCTCGCGCTCTGCCCAGGAGGCCCCGGCGGCCTCGGCG
ATCCCCTGCGAGCGCTGCTGCTCCTGAAGGCGCTGCAGGGCCTGCGCGTG
GAGTGGCGCGGGCGGGATCCGCGCGGGCCGGGTCGGGCACAGCGCAGCGC
GGGGGCCACCGCCGCCGACGGGCCGTGCGCTGCGCGAGCTCAGCGTAG
ACCTCCGCGCCGAGCGCTCCGTACTCATCCCCGAGACCTACCAGGCCAAC
AATTGCCAGGGCGTGTGCGGCTGGCCTCAGTCCGACCGCAACCCGCGCTA
CGGCAACCACGTGGTGCTGCTGCTGAAGATGCAGGCCCGTGGGGCCGCCC
TGGCGCGCCCACCCTGCTGCGTGCCCACCGCCTACGCGGGCAAGCTGCTC
ATCAGCCTGTCGGAGGAACGCATCAGCGCGCACCACGTGCCCAACATGGT
GGCCACCGAGTGTGGCTGCCGGTGACCCCTGCGCCGCGCGGACTCCTGCC
CCGAGGGTCCGGACGCGCCCCAGCTCGCGCCCCTTCCCATATTTATTCGG
ACCCCAAGCATCGCCCCAATAAAGACCAGCAAGC;
AGCACCCACGATGCGGGACCTGCCTCTCACCAGCCTGGCCCTAGTGCTGT
CTGCCCTGGGGGCTCTGCTGGGGACTGAGGCCCTCAGAGCAGAGGAGCCA
GCTGTGGGCACCAGTGGCCTCATCTTCCGAGAAGACTTGGACTGGCCTCC
AGGCATCCCACAAGAGCCTCTGTGCCTGGTGGCACTGGGCGGGGACAGCA
ATGGCAGCAGCTCCCCCCTGCGGGTGGTGGGGCTCTAAGCGCCTATGAG
CAGGCCTTCCTGGGGGCCGTGCAGAGGGCCCGCTGGGGCCCCCGAGACCT
GGCCACCTTCGGGGTCTGCAACACCGGTGACAGGCAGGCTGCCTTGCCCT
CTCTACGGCGGCTGGGGGCCTGGCTGCGGGACCCTGGGGGGCAGCGCCTG
GTGGTCCTACACCTGGAGGAAGGTGACCTGGGAGCCAACACCCTCGCTGAG
GTTCCAGGAGCCCCCGCCTGGAGGAGCTGGCCCCCAGAGCTGGCGCTGC
TGGTGCTGTACCCTGGGCCTGGCCCTGAGGTCACTGTGACGAGGGCTGGG
CTGCCGGGTGCCCAGAGCCTCTGCCCCTCCCGAGACACCCGCTACCTGGT
GTTAGCGGTGGACCGCCCTGCGGGGGCCTGGCGGCTCCGGGCTGGCCT
TGACCCTGCAGCCCCGCGGAGAGGACTCCCGGCTGAGTACCGCCCGGCTG
CAGGCACTGCTGTTCGGCGACGACCACCGCTGCTTCACACGGATGACCCC
GGCCCTGCTCCTGCTGCCGCGGTCCGAGCCCGCGCCGCTGCCTGCGCACG
GCCAGCTGGACACCGTGCCCTTCCCGCCGCCCAGGCCATCCGCGGAACTC
GAGGAGTCGCCACCCAGCCAGACCCCTTCCTGGAGACGCTCACGCGCCT
GGTGCGGGCGCTGCGGGTCCCCCCGGCCCGGGCCTCCGCGCCGCGCCTGG
CCCTGGATCCGGACGCGCTGGCCGGCTTCCCGCAGGGCCTAGTCAACCTG
TCGGACCCCGCGGCGCTGGAGCGCCTACTCGACGGCGAGGAGCCGCTGCT
GCTGCTGCTGAGGCCCACTGCGGCCACCACCGGGGATCCTGCGCCCCTGC
```

-continued

```
ACGACCCCACGTCGGCGCCGTGGGCCACGGCCCTGGCGCGCCGCGTGGCT
GCTGAACTGCAAGCGGCGGCTGCCGAGCTGCGAAGCCTCCCGGGTCTGCC
TCCGGCCACAGCCCCGCTGCTGGCGCGCCTGCTCGCGCTCTGCCCAGGAG
GCCCCGGCGGCCTCGGCGATCCCCTGCGAGCGCTGCTGCTCCTGAAGGCG
CTGCAGGGCCTGCGCGTGGAGTGGCGCGGGCGGGATCCGCGCGGGCCGGG
TCGGGCACAGCGCAGCGCGGGGGCCACCGCCGCCGACGGGCCGTGCGCGC
TGCGCGAGCTCAGCGTAGACCTCCGCGCCGAGCGCTCCGTACTCATCCCC
GAGACCTACCAGGCCAACAATTGCCAGGGCGTGTGCGGCTGGCCTCAGTC
CGACCGCAACCCGCGCTACGGCAACCACGTGGTGCTGCTGCTGAAGATGC
AGGCCCGTGGGGCCGCCCTGGCGCGCCCACCCTGCTGCGTGCCCACCGCC
TACGCGGGCAAGCTGCTCATCAGCCTGTCGGAGGAACGCATCAGCGCGCA
CCACGTGCCCAACATGGTGGCCACCGAGTGTGGCTGCCGGTGACCCCTGC
GCCGCGCGGACTCCTGCCCCGAGGGTCCGGACGCGCCCCAGCTCGCGCCC
CTTCCCATATTTATTCGGACCCCAAGCATCGCCCCAATAAAGACCAGCAA
GC;
CAAGGTCATGTCCCAGGAGGAGATAGGGACCGCCCTGCACCACAAACAGC
TCTGCTCCCTCTTATAAAGTAGGGCAGCCCAGCCCCTGGAAGCTCCCAGG
ATGCCCGGTCCATCTCTCTCTCTGGCCCTGGTGCTGTCGGCCATGGGGGC
TCTGCTGAGGCCAGGGACCCCCAGGGAAGAAGTCTTCAGCACCTCAGCCT
TGCCCAGGGAGCAGGCCACAGGCAGCGGGGCACTCATCTTTCAGCAAGCC
TGGGACTGGCCACTCTCCAGTCTCTGGCTGCCAGGCAGCCCTCTGGACCC
CCTGTGCCTGGTGACCCTGCATGGGAGTGGCAACGGGAGCAGGGCCCCCC
TGCGGGTGGTGGGGGTCCTGAGCAGCTACGAGCAGGCCTTCCTGGAGGCT
GTGCGGCGCACCCACTGGGGCCTGAGTGACTTGACCACCTTCGCAGTGTG
CCCCGCTGGCAACGGGCAGCCTGTGCTGCCCCACCTGCAGCGGCTGCAGG
CATGGCTGGGGGAGCCCGGGGGGCGGTGGCTGGTGGTCCTGCACCTGGAG
GAAGTGACGTGGGAGCCAACACCCTTGCTGAGGTTCCAGGAGCCTCCGCC
TGGAGGAGCCAGCCCCCAGAGCTGGCGCTGCTGGTGGTGTACCCAGGGC
CTGGCCTGGAGGTCACTGTCACCGGGGCTGGGCTACCTGGCACCCAGAGC
CTCTGCCTGACCGCGGACTCGGACTTCCTGGCCTTGGTCGTGGACCACCC
GGAGGGGGCCTGGCGCCGGCCTGGGTTAGCCCTTACCCTGCGGCGCCGTG
GAAATGGTGCGCTCCTGAGCACTGCCCAGCTGCAGGCGCTGCTGTTCGGT
GCGGACTCCCGCTGCTTCACACGAAAGACCCCAGCCCTGTTACTCTTGCT
GCCGGCCCGGTCTTCGGCACCGATGCCCGCGCACGGTCGGCTGGACTTGG
TGCCCTTCCCGCAGCCCAGGGCTTCCCCGGAGCCAGAGGAGGCACCGCCC
AGCGCTGATCCCTTCCTGGAGACTCTCACGCGCCTGGTGCGCGCGCTTGC
GGGACCCCCGGCCCGAGCCTCGCCACCGCGGCTGGCCTTGGACCCGGGCG
CACTGGCTGGTTTCCCGCAGGGCCAGGTCAACCTGTCGGACCCCGCGGCC
CTGGAGCGCCTGCTGGACGGCGAGGAGCCGCTGCTGCTGCTGCCGCC
GACGGCAGCCACCACCGGGGTCCCCGCAACGCCGCAAGGTCCCAAGTCCC
CTCTGTGGGCCGCGGACTAGCGCGCCGGGTGGCTGCCGAGCTTCAGGCG
GTGGCCGCCGAGCTGCGTGCCCTCCCGGGGCTGCCTCCAGCTGCCCCACC
GCTGCTGGCCGCGCTGCTGGCACTGTGCCCGGGAAACCCAGACAGCCCCG
GCGGCCCGCTGCGCGCGCTGCTGCTGCTCAAAGCGCTGCAGGGCCTGCGC
GCTGAGTGGCGCGGGCGGGAGCGGAGCGGCTCTGCACGGGCGCAGCGCAG
CGCCGGGGCCGCGGCTGCAGACGGGCCGTGCGCTCTGCGTGAGCTGAGCG
TAGACCTGCGGGCCGAGCGCTCGGTGCTCATCCCCGAGACATACCAGGCC
AACAACTGCCAGGGGGCCTGCGGCTGGCCTCAGTCGGACCGCAACCCGCG
CTACGGCAACCACGTGGTGCTGCTGCTAAAGATGCAGGCCCGCGGCGCCA
CCCTGGCGCGCCCGCCCTGCTGTGTGCCCACAGCCTACACCGGCAAGCTC
CTCATCAGCCTGTCCGAGGAGCGCATCAGTGCGCACCACGTCCCAAACAT
GGTGGCCACCGAATGCGGCTGCCGGTGACCTCGCCGCCGTGCTCCTCGTGC
TGCCCCGGCCCGTATTTATTCGGACCCCGTCATTGCCCCATTAAACACGG
GAAGGC; and
AGCTCCCAGGATGCCCGGTCCATCTCTCTCTCTGGCCCTGGTGCTGTCGG
CCATGGGGGCTCTGCTGAGGCCAGGGACCCCCAGGGAAGAAGTCTTCAGC
ACCTCAGCCTTGCCCAGGGAGCAGGCCACAGGCAGCGGGGCACTCATCTT
TCA3CAAGCCTGGGACTGGCCACTCTCCAGTCTCTGGCTGCCAGGCAGCC
CTCTGGACCCCCTGTGCCTGGTGACCCTGCATGGGAGTGGCAACGGGAGC
AGGGCCCCCCTGCGGGTGGTGGGGGTCCTGAGCAGCTACGAGCAGGCCTT
CCTGGAGGCTGTGCGGCGCACCCACTGGGGCCTGAGTGACTTGACCACCT
TCGCAGTGTGCCCCGCTGGCAACGGGCAGCCTGTGCTGCCCCACCTGCAG
CGGCTGCAGGCATGGCTGGGGGAGCCCGGGGGGCGGTGGCTGGTGGTCCT
GCACCTGGAGGAAGTGACGTGGGAGCCAACACCCTTGCTGAGGTTCCAGG
AGCCTCCGCCTGGAGGAGCCAGCCCCCAGAGCTGGCGCTGCTGGTGGTG
TACCCAGGGCCTGGCCTGGAGGTCACTGTCACCGGGGCTGGGCTACCTGG
CACCCAGAGCCTCTGCCTGACCGCGGACTCGGACTTCCTGGCCTTGGTCG
TGGACCACCCGGAGGGGGCCTGGCGCCGGCCTGGGTTAGCCCTTACCCTG
CGGCGCCGTGGAAATGGTGCGCTCCTGAGCACTGCCCAGCTGCAGGCGCT
GCTGTTCGGTGCGGACTCCCGCTGCTTCACACGAAAGACCCCAGCCCTGT
TACTCTTGCTGCCGGCCCGGTCTTCGGCACCGATGCCCGCGCACGGTCGG
CTGGACTTGGTGCCCTTCCCGCAGCCCAGGGCTTCCCCGGAGCCAGAGGA
GGCACCGCCCAGCGCTGATCCCTTCCTGGAGACTCTCACGCGCCTGGTGC
GCGCGCTTGCGGGACCCCCGGCCCGAGCCTCGCCACCGCGGCTGGCCTTG
GACCCGGGCGCACTGGCTGGTTTCCCGCAGGGCCAGGTCAACCTGTCGGA
CCCCGCGGCCCTGGAGCGCCTGCTGGACGGCGAGGAGCCGCTGCTGCTGC
TGCTGCCGCCGACGGCAGCCACCACCGGGGTCCCCGCAACGCCGCAAGGT
CCCAAGTCCCCTCTGTGGGCCGCGGACTAGCGCGCCGGGTGGCTGCCGA
GCTTCAGGCGGTGGCCGCCGAGCTGCGTGCCCTCCCGGGGCTGCCTCCAG
CTGCCCCACCGCTGCTGGCGCGCCTGCTGGCACTGTGCCCGGGAAACCCA
GACAGCCCCGGCGGCCCGCTGCGCGCGCTGCTGCTGCTCAAAGCGCTGCA
GGGCCTGCGCGCTGAGTGGCGCGGGCGGGAGCGGAGCGGCTCTGCACGGG
CGCAGCGCAGCGCCGGGGCCGCGGCTGCAGACGGGCCGTGCGCTCTGCGT
```

-continued
```
GAGCTGAGCGTAGACCTGCGGGCCGAGCGCTCGGTGCTCATCCCCGAGAC
ATACCAGGCCAACAACTGCCAGGGGGCCTGCGGCTGGCCTCAGTCGGACC
GCAACCCGCGCTACGGCAACCACGTGGTGCTGCTGCTAAAGATGCAGGCC
CGCGGCGCCACCCTGGCGCGCCCGCCCTGCTGTGTGCCCACAGCCTACAC
CGGCAAGCTCCTCATCAGCCTGTCCGAGGAGCGCATCAGTGCGCACCACG
TCCCAAACATGGTGGCCACCGAATGCGGCTGCCGGTGACCTCGCGCCGTG
CTCCTCGTGCTGCCCCGGCCCGTATTTATTCGGACCCCGTCATTGCCCCA
TTAAACACGGGAAGGC
```

2. A recombinant DNA molecule comprising a DNA sequence selected from the group consisting of:
  (a) the DNA sequences of claim 1;
  (b) DNA sequences that hybridize to any of the DNA sequences of (a) and that code for a polypeptide displaying the biological or immunological activity of a human or bovine MIS protein; and
  (c) DNA sequences which are degenerate as a result of the genetic code to the DNA sequences defined above and which code for a polypeptide displaying the biological or immunological activity of a human or bovine MIS protein.

3. The recombinant DNA molecule according to claim 2, wherein said DNA sequence is operatively linked to an expression control sequence in the recombinant DNA molecule.

4. The recombinant DNA molecule according to claim 3, wherein said expression control sequence is selected from the group consisting of the early and late promoters of SV40, the lac system, the tac system, the trc system, the trp system, adenovirus major late promoter, major operator and promotor regions of phage λ, the control regions of fd coat protein, the promoter of 3-phosphoglycerate kinase or other glycolytic enzymes, the promoters of acid phosphatase, the promoters of yeast α-mating factors, and other sequences which control the expression of genes of prokaryotic or eukaryotic cells or their viruses.

5. A host transformed with the recombinant DNA molecule of claim 4.

6. A host transformed with the recombinant DNA molecule of claim 3.

7. The recombinant DNA molecule according to claim 3, selected from the group consisting of pBG311.bmis, pBG311.hmis and pBG312.hmis.

8. A host transformed with the recombinant DNA molecule of claim 7.

9. A host transformed with the recombinant DNA molecule of claim 2.

10. A host transformed with the recombinant DNA molecule of claim 2, said host being selected from the group consisting of strains of *E.coli*, Pseudomonas, Bacillus, yeast and animal cells in culture.

11. The host according to claim 10, wherein said animal cells are selected from the group consisting of COS cells, CHO cells, mouse cells, swine cells and human tissue cells in culture.

12. A method of producing a polypeptide displaying the biological or immunological activity of an MIS protein, said method comprising the step of culturing a host transformed with a recombinant DNA molecule according to claim 3.

13. The method according to claim 12, wherein said recombinant DNA molecule is selected from the group consisting of pBG311.bmis, pBG311.hmis, and pBG312.hmis.

14. The method according to claim 12, wherein said host comprises strains of *E.coli*, Pseudomonas, Bacillus, yeast and animal cells in culture.

15. The method according to claim 14, wherein said animal cells are selected from the group consisting of COS cells, CHO cells, mouse cells, swine cells, and human tissue cells in culture.

* * * * *